(12) United States Patent
Iwasaki et al.

(10) Patent No.: US 11,446,255 B2
(45) Date of Patent: Sep. 20, 2022

(54) SHEET, SHEET LAMINATE, PHARMACEUTICAL DRUG, SHEET PRODUCING METHOD, SHEET PRODUCING APPARATUS, SHEET LAMINATE PRODUCING METHOD, AND SHEET LAMINATE PRODUCING APPARATUS

(71) Applicant: RICOH COMPANY, LTD., Tokyo (JP)

(72) Inventors: Koji Iwasaki, Kanagawa (JP); Toshihiro Kanematsu, Kanagawa (JP); Rie Kobayashi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 50 days.

(21) Appl. No.: 16/813,037

(22) Filed: Mar. 9, 2020

(65) Prior Publication Data
US 2020/0297653 A1   Sep. 24, 2020

(30) Foreign Application Priority Data

Mar. 20, 2019   (JP) ............... JP2019-052246

(51) Int. Cl.
| | |
|---|---|
| *A61K 9/70* | (2006.01) |
| *A61K 31/122* | (2006.01) |
| *A61K 31/525* | (2006.01) |
| *A61K 47/34* | (2017.01) |
| *A61K 47/42* | (2017.01) |

(52) U.S. Cl.
CPC .......... *A61K 9/7007* (2013.01); *A61K 31/122* (2013.01); *A61K 31/525* (2013.01); *A61K 47/34* (2013.01); *A61K 47/42* (2013.01)

(58) Field of Classification Search
None
See application file for complete search history.

(56) References Cited

U.S. PATENT DOCUMENTS

| | | | | |
|---|---|---|---|---|
| 5,348,788 | A | 9/1994 | White | |
| 2008/0175911 | A1* | 7/2008 | McKay | A61K 38/1875 424/489 |
| 2008/0220204 | A1 | 9/2008 | Ohgaki et al. | |
| 2009/0133804 | A1 | 5/2009 | Kanematsu et al. | |
| 2010/0129527 | A1 | 5/2010 | Ohshima et al. | |
| 2010/0188731 | A1 | 7/2010 | Kanematsu et al. | |
| 2010/0326020 | A1 | 12/2010 | Schmaelzle et al. | |
| 2011/0001277 | A1 | 1/2011 | Kanematsu et al. | |
| 2012/0009159 | A1* | 1/2012 | Humayun | A61K 35/545 424/93.7 |
| 2012/0027833 | A1* | 2/2012 | Zilberman | A61K 31/546 424/422 |
| 2012/0114876 | A1 | 5/2012 | Kanematsu et al. | |
| 2015/0119807 | A1* | 4/2015 | Desai | G03F 7/0035 604/175 |
| 2015/0306539 | A1 | 10/2015 | Yamato | |
| 2018/0201713 | A1 | 7/2018 | Iwasaki | |
| 2018/0275433 | A1 | 9/2018 | Iwasaki | |

FOREIGN PATENT DOCUMENTS

| | | |
|---|---|---|
| CN | 104999745 | 10/2015 |
| JP | 57-004918 | 1/1982 |
| JP | 57-139011 | 8/1982 |
| JP | 59-059734 | 4/1984 |
| JP | 61-030517 | 2/1986 |
| JP | 61-280423 | 12/1986 |
| JP | 62-142113 | 6/1987 |
| JP | 62-207208 | 9/1987 |
| JP | 2-059513 | 2/1990 |
| JP | 2-250826 | 10/1990 |
| JP | 2001-288074 | 10/2001 |
| JP | 2001-302500 | 10/2001 |
| JP | 2003-095947 | 4/2003 |
| JP | 2004-196784 | 7/2004 |
| JP | 2005-289941 | 10/2005 |
| JP | 2005-342154 | 12/2005 |
| JP | 2006-511543 | 4/2006 |
| JP | 2006-193458 | 7/2006 |
| JP | 2006-199660 | 8/2006 |
| JP | 2007-098930 | 4/2007 |
| JP | 2007-277190 | 10/2007 |
| JP | 2008-072915 | 4/2008 |
| JP | 2009-507854 | 2/2009 |
| JP | 2009-214374 | 9/2009 |
| JP | 2009-215305 | 9/2009 |
| JP | 2009-275055 | 11/2009 |
| JP | 2010-132653 | 6/2010 |

(Continued)

OTHER PUBLICATIONS

Chinese Office Action dated Dec. 20, 2021 in Chinese Application 202010180740.3, 6 pages.
Partial European Search Report dated Aug. 24, 2020 in corresponding European Patent Application No. 20159411.6, 11pages.

* cited by examiner

*Primary Examiner* — Katherine Peebles
(74) *Attorney, Agent, or Firm* — Grüneberg and Myers PLLC

(57) ABSTRACT

Provided is a sheet including a base material comprising a biocompatible material and having at least two independent holes, and a bioactive substance, wherein at least one of the independent holes is an independent hole A containing the bioactive substance, wherein at least one of the independent holes is an independent hole B containing no bioactive substance, wherein a maximum diameter of the independent holes is less than 0.2 mm. Also provided is a sheet laminate including sheets laminated with each other, wherein each of the sheets includes a base material comprising a biocompatible material and having at least two independent holes, and a bioactive substance, wherein at least one of the independent holes is an independent hole A containing the bioactive substance, wherein at least one of the independent holes is an independent hole B containing no bioactive substance.

16 Claims, 12 Drawing Sheets

(56) References Cited

FOREIGN PATENT DOCUMENTS

| | | |
|---|---|---|
| JP | 2010-207613 | 9/2010 |
| JP | 2013-099342 | 5/2013 |
| JP | 2013-527198 | 6/2013 |
| JP | 2013-147459 | 8/2013 |
| JP | 2014-196315 | 10/2014 |
| JP | 2014-227391 | 12/2014 |
| JP | 2016-507485 | 3/2016 |
| JP | 2016-513736 | 5/2016 |
| JP | 2017-043607 | 3/2017 |
| JP | 2018-145128 | 9/2018 |
| WO | WO2004/054547 A1 | 7/2004 |
| WO | WO2006/059701 A1 | 6/2006 |
| WO | WO 2007/029864 A1 | 3/2007 |
| WO | WO2007/030754 A2 | 3/2007 |
| WO | WO2007/083698 A1 | 7/2007 |
| WO | WO 2009/113705 A1 | 9/2009 |
| WO | WO2011/150306 A1 | 12/2011 |
| WO | WO2012/137610 A1 | 10/2012 |
| WO | WO2014/088181 A1 | 6/2014 |
| WO | WO2014/144241 A1 | 9/2014 |
| WO | WO-2017160850 A1 * | 9/2017 ............. B81B 1/008 | ized by the cross-references in the page header.

SHEET, SHEET LAMINATE, PHARMACEUTICAL DRUG, SHEET PRODUCING METHOD, SHEET PRODUCING APPARATUS, SHEET LAMINATE PRODUCING METHOD, AND SHEET LAMINATE PRODUCING APPARATUS

CROSS-REFERENCE TO RELATED APPLICATIONS

This patent application is based on and claims priority pursuant to 35 U.S.C. § 119(a) to Japanese Patent Application No. 2019-052246, filed on Mar. 20, 2019, in the Japan Patent Office, the entire disclosure of which is hereby incorporated by reference herein.

BACKGROUND

Technical Field

The present disclosure relates to a sheet, a sheet laminate, a pharmaceutical drug, a sheet producing method, a sheet producing apparatus, a sheet laminate producing method, and a sheet laminate producing apparatus.

Description of the Related Art

Hitherto, in the field of pharmaceutical production, pharmaceutical drugs each containing a plurality of kinds of bioactive substances have been produced.

Such pharmaceutical drugs that have been proposed include a pharmaceutical composition obtained by modeling particles of a pharmaceutical composition containing one or more kinds of bioactive substances, using a powder additive manufacturing-type three-dimensional object producing method, in order to provide a rapidly dispersible dosage form.

Another proposed example is a laminated film obtained by sequentially laminating a gastric-soluble film and an enteric film each containing a pharmacologically active substance that releases one or more kinds of substances depending on the ambient conditions.

SUMMARY

According to an aspect of the present disclosure, a sheet includes a base material comprising a biocompatible material and having at least two independent holes, and a bioactive substance. The independent holes include at least one independent hole A containing the bioactive substance. The independent holes include at least one independent hole B containing no bioactive substance. The maximum diameter of the independent holes is less than 0.2 mm.

BRIEF DESCRIPTION OF THE SEVERAL VIEWS OF THE DRAWINGS

A more complete appreciation of the disclosure and many of the attendant advantages and features thereof can be readily obtained and understood from the following detailed description with reference to the accompanying drawings, wherein.

Figure 1A:
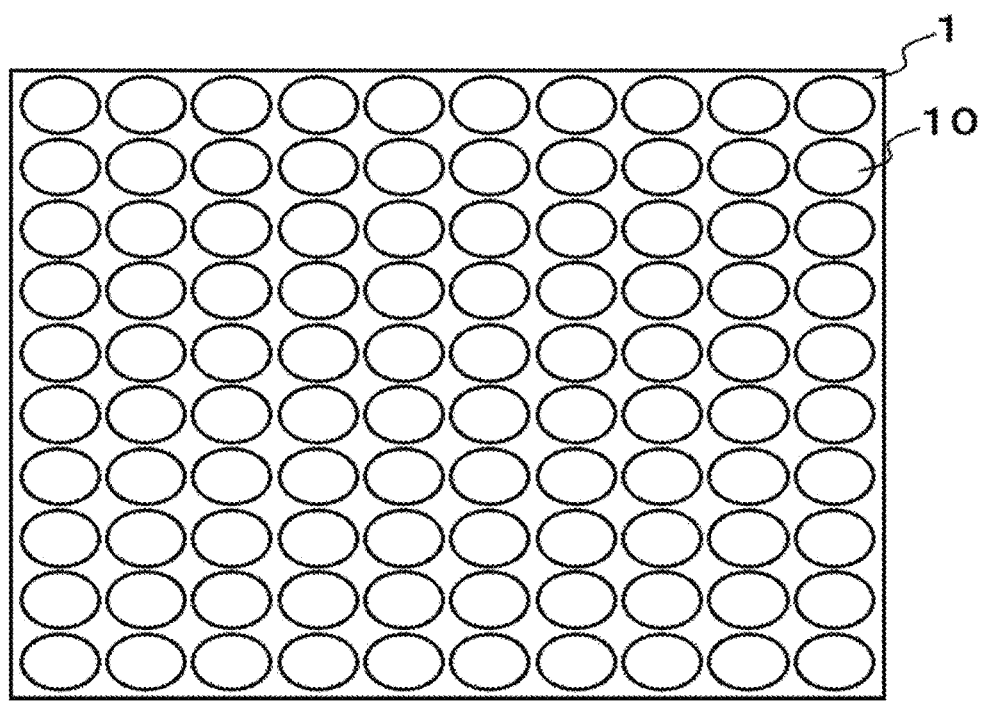
FIG. 1A is a view illustrating an exemplary arrangement of independent holes in a base material of a sheet according to an embodiment of the present disclosure.

The accompanying drawings are intended to depict embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

According to the present disclosure, it is possible to provide a sheet that can contain a plurality of bioactive substances in a mutually non-mixed state in high contents per unit number, has a sufficient mechanical strength as a dosage form before administration, and has an excellent water disintegrability.

(Sheet)

A sheet of the present disclosure includes a base material having at least two independent holes, and a bioactive substance. The independent holes include at least one independent hole A containing the bioactive substance. The independent holes include at least one independent hole B containing no bioactive substance. The maximum diameter of the independent holes is less than 0.2 mm. The base material contains a biocompatible material, and further contains other components as needed.

The inventors of the present invention have obtained the following finding as a result of studying a sheet that can contain a plurality of bioactive substances in a mutually non-mixed state in high contents per unit number, has a sufficient mechanical strength as a dosage form before administration, and has an excellent water disintegrability.

Specifically, when pharmaceutical compositions each containing a plurality of bioactive substances are produced by modelling using existing powder additive manufacturing-type three-dimensional object producing methods, there is a problem that the bioactive substances contained in the voids in the pharmaceutical compositions physically contact and mix with each other because the voids have no anisotropy, and as a result the bioactive substances react chemically and denature before administration.

Existing laminated films also have a problem that bioactive substances cannot be contained in high contents due to limitation on the number of layers that can be laminated, because increasing the number of layers to be laminated increases the mechanical strength but degrades the water disintegrability.

Hence, the inventors of the present invention have produced a sheet that includes a base material having at least two independent holes, with an independent hole containing a bioactive substance and an independent hole containing no bioactive substance. With the configuration described above, the sheet of the present disclosure can prevent bioactive substances contained in the independent holes from contacting and mixing with each other, and can contain bioactive substances in higher contents per sheet. The sheet of the present disclosure also has an excellent water disintegrability regardless of a sufficient mechanical strength as a dosage form before administration, because independent holes containing no bioactive substances easily disintegrate in water.

<Base Material>

The base material includes at least two independent holes. At least one of the independent holes is an independent hole A containing a bioactive substance. At least one of the independent holes is an independent hole B containing no bioactive substance. The maximum diameter of the independent holes is less than 0.2 mm. The base material contains a biocompatible material.

The base material is not particularly limited and may be appropriately selected depending on the intended purpose as long as the base material contains a biocompatible material. The base material may be a product appropriately produced or may be a commercially available product. Examples of the method for producing the base material include, but are not limited to, a method of dissolving a material containing a biocompatible material in water to form a molding liquid, applying the molding liquid on the entire surface of a flat plate, and volatilizing the water. In the sheet of the present disclosure, it is preferable to add a plasticizer in the molding liquid in order to suppress cracking of the base material. The plasticizer is not particularly limited and may be appropriately selected depending on the intended purpose. Examples of the plasticizer include, but are not limited to, glycerin.

—Independent Holes—

The independent holes are holes separated from each other. The shape and size of the independent holes are not particularly limited and may be appropriately selected depending on the intended purpose as long as the maximum diameter of the openings of the independent holes is less than 0.2 mm.

The maximum diameter of the openings of the independent holes refers to the length of the longest line segment among line segments that pass the center of the hole shape of the openings of the holes to extend from a point on the perimeter of the hole to another point on the perimeter of the hole.

—Independent Hole A—

The independent hole A is an independent hole containing a bioactive substance, and may further contain other components as needed.

[Bioactive Substances]

The bioactive substances are not particularly limited and may be appropriately selected depending on the intended purpose. Examples of the bioactive substances include, but are not limited to, main nutrients needed for life-sustaining activities; vitamins as the generic term of organic compounds essential for normal growth of animals; hormones that are organic compounds produced in specified organs or cells of living organisms and express specific physiological effects even to organs apart from the tissues in which the hormones are produced; pheromones that are secreted from living organisms of some species and act on another individual of the same species to induce actions such as assembling and mating; antibiotics that are substances produced by microbes and inhibit growth or metabolism of other microbes; and chemically synthesized drugs. One of these bioactive substances may be used alone or two or more of these bioactive substances may be used in combination as long as they satisfy conditions described below.

Other examples of the bioactive substances than those mentioned above include, but are not limited to, pharmaceutical compounds, functional food compounds, and functional cosmetic compounds.

—Pharmaceutical Compounds—

The pharmaceutical compounds used for pharmaceutical drugs are not particularly limited and may be appropriately selected depending on the intended purpose.

The pharmaceutical compounds are not particularly limited and may be appropriately selected depending on the intended purpose. Examples of the pharmaceutical compounds include, but are not limited to, abacavir, acetaminophen, acyclovir, amiloride, amitriptyline, antipyrine, atropine, buspirone, caffeine, captopril, chloroquine, chlorpheniramine, cyclophosphamide, desipramine, diazepam, diltiazem, diphenhydramine, disopyramide, doxin, doxycycline, enalapril, ephedrine, ethambutol, ethinylestradiol, fluoxetine, imipramine, clomipramine, glucose, ketorol, ketoprofen, labetalol, levodopa, levofloxacin, metoprolol, metronidazole, midazolam, minocycline, misoprostol, metformin, nifedipine, phenobarbital, prednisolone, promazine, propranolol, quinidine, rosiglitazone, salicylic acid, theophylline, valproic acid, verapamil, zidovudine, and calcitonin. One of these pharmaceutical compounds may be used alone or two or more of these pharmaceutical compounds may be used in combination.

—Functional Food Compounds—

The functional food compounds are not particularly limited and may be appropriately selected depending on the intended purpose. Examples of the functional food compounds include, but are not limited to, vitamin A, vitamin D, vitamin E, lutein, zeaxanthin, lipoic acid, flavonoid, and fatty acids (e.g., omega-3 fatty acid and omega-6 fatty acid). One of these functional food compounds may be used alone or two or more of these functional food compounds may be used in combination.

—Functional Cosmetic Compounds—

The functional cosmetic compounds are not particularly limited and may be appropriately selected depending on the intended purpose. Examples of the functional cosmetic compounds include, but are not limited to, alcohols, fatty alcohols, polyols, aldehydes, alkanol amines, alkoxylated alcohols (e.g., polyethylene glycol derivatives of alcohols and fatty alcohols), alkoxylated amides, alkoxylated amines, alkoxylated carboxylic acids, amides containing salts (e.g., ceramides), amines, amino acids containing salts and alkyl-substituted derivatives, esters, alkyl-substituted and acyl derivatives, polyacrylic acids, acrylamide copolymers, adipic acid copolymer water, amino silicones, biological polymers and derivatives of biological polymers, butylene copolymers, hydrocarbons (e.g., polysaccharides, chitosan, and derivatives of polysaccharides and chitosan), carboxylic acids, carbomers, ethers and polymer ethers (e.g., PEG derivatives and PPG derivatives), glyceryl esters and derivatives of glyceryl esters, halogen compounds, heterocyclic compounds containing salts, hydrophilic colloids and salt or rubber-containing derivatives of hydrophilic colloids (e.g., cellulose derivatives, gelatin, xanthan gum, and natural rubber), imidazolines, inorganic substances (e.g., clay, $TiO_2$, and ZnO), ketones (e.g., camphor), isethionates, lanolin and derivatives of lanolin, organic salts, phenols containing salts (e.g., parabens), phosphorus compounds (e.g., phosphoric acid derivatives), polyacrylates and acrylate copolymers, proteins and enzyme derivatives (e.g., collagen), synthetic polymers containing salts, siloxanes and silanes, sorbitan derivatives, sterols, sulfonic acid and derivatives of sulfonic acid, and waxes. One of these functional cosmetic compounds may be used alone or two or more of these functional cosmetic compounds may be used in combination.

The content of the bioactive substance contained in the independent hole A is not particularly limited and may be appropriately selected depending on the kind of the bioactive sub stance.

Examples of the other components include, but are not limited to, an antioxidant, a pH adjustor, a surfactant, water, and ethanol, for stabilization of the bioactive substances.

The bioactive substances contained in the independent holes A may be varied between one independent hole $A_1$ and another independent hole $A_2$. With different bioactive substances contained in an independent hole $A_1$ and another independent hole $A_2$, different kinds of substances can be carried in one drug to be administered, without being mixed with each other before use. This configuration also allows intake of many kinds of substances by one drug to be administered, when there is a need for administering many kinds of substances per administration.

It is preferable that the independent holes A be arranged in the sheet in a manner that, for example, when one independent hole A is an independent hole $A_1$ containing a first bioactive substance and another independent hole A located closest to the one independent hole A is an independent hole $A_2$ containing a second bioactive substance different from the first bioactive substance, one or more other independent holes are arranged between the one independent hole A and the another independent hole A. By arranging independent holes containing different kinds of bioactive substances at physically separated locations, it is possible to avoid contacting and mixing of the bioactive substances more reliably.

It is more preferable that an independent hole B and an independent hole C described below be arranged between the independent hole $A_1$ containing the first bioactive substance and the independent hole $A_2$ containing the second bioactive substance. With the independent hole B and the independent hole C described below arranged between the independent hole $A_1$ containing the first bioactive substance and the independent hole $A_2$ containing the second bioactive substance, it is possible to avoid contacting and mixing of the different kinds of bioactive substances more reliably.

The distance between the independent hole $A_1$ and the independent hole $A_2$ may be appropriately selected depending on the size of the base material in which the holes are formed. For example, the distance between the centers of the holes is preferably 0.2 mm or greater, more preferably 1.0 mm or greater, and yet more preferably 1.8 mm or greater.

—Independent Hole B—

The independent hole B is an independent hole containing no bioactive substance.

Containing no bioactive substance means containing a substance other than a bioactive substance.

The substance other than a bioactive substance is not particularly limited and may be appropriately selected depending on the intended purpose. Examples of the substance other than a bioactive substance include, but are not limited to, a foaming agent and a swelling agent for improvement of water disintegrability.

It is preferable that the independent hole B be a hollow concave. An independent hole B that is a hollow concave makes the sheet easily disintegrable because body fluids flow into the independent hole B when the sheet is administered into a living body.

It is preferable that the sheet of the present disclosure further include an independent hole C containing a thermoplastic material.

—Independent Hole C—

The independent hole C is an independent hole containing a thermoplastic material. With the independent hole C, the sheet can be increased in mechanical strength.

[Thermoplastic Material]

The thermoplastic material is not particularly limited and may be appropriately selected depending on the intended purpose. The thermoplastic material may be freely selected from materials that plasticize at a predetermined temperature or materials that change to a rubber state in a predetermined temperature range depending on the application of the sheet, which is one of the embodiments of the present disclosure. The thermoplastic material is preferably, for example, a material that can be used as an additive for pharmaceutical drugs without any problem. Materials such as gelatin, agar, polyethylene glycol and modified bodies of polyethylene glycol, polyvinyl alcohol and modified bodies of polyvinyl alcohol, polyvinyl pyrrolidone and modified bodies of polyvinyl pyrrolidone, and acrylic elastomers are more preferable. One of these thermoplastic materials may be used alone or two or more of these thermoplastic materials may be used in combination.

In the sheet of the present disclosure, the ratio of the number of independent holes B to the number of all independent holes is preferably 5% or greater but 90% or less and more preferably 40% or greater but 60% or less. When the ratio of the number of independent holes B is less than 5%, the strength of the sheet is low. When the ratio of the number of independent holes B is greater than 90%, the water disintegration speed is low.

The ratio of the number of independent holes C is preferably 5% or greater but 90% or less, more preferably 10% or greater but 90% or less, and more preferably 20% or greater but 80% or less. When the ratio of the number of independent holes C is less than 5%, the water integration speed is low. When the ratio of the number of independent holes C is greater than 90%, the strength of the sheet is low.

The sum of the ratio of the number of independent holes B and the ratio of the number of independent holes C is preferably 20% or greater but less than 100%. Because the ratio of the independent holes B and the ratio of the independent holes C conflict with each other, the sum D of the ratio of the number of independent holes B and the ratio of the number of independent holes C is preferably 20% or greater but less than 100% in the present disclosure. When the sum D is in this range, mechanical strength and water disintegrability can be balanced.

It is preferable that the sheet of the present disclosure include a brittle portion in the base material.

The brittle portion is not particularly limited and may be appropriately selected depending on the intended purpose as long as the brittle portion is designed to be have a lower mechanical strength than other portions of the base material constituting the sheet. Examples of the brittle portion include, but are not limited to, a perforated portion provided at other than the independent holes, and the independent holes B that are hollow concaves described above. With the brittle portion in the sheet, the sheet rapidly disintegrates after administered into a living body, and the bioactive substances contained in the sheet can be rapidly released.

It is preferable that the brittle portion be provided in a manner to be arranged in a predetermined shape in the sheet, in order to make it easier to form the sheet into a predetermined shape.

Formation of the brittle portion or punching may be applied to the sheet in which the independent holes are formed or to a sheet laminate described below. That is, such processing may be applied after the independent holes are formed or after a laminate is formed. Formation of the brittle portion or punching may be selected depending on the application.

—Biocompatible Material—

The biocompatible material is not particularly limited and may be appropriately selected depending on the intended purpose as long as the biocompatible material is a material that is intended to interact with a living body and induces an appropriate response in a living body. Examples of the appropriate response include, but are not limited to, occurrence of almost no response to a foreign matter. The biocompatible material is preferably, for example, a material that can be used as an additive for pharmaceutical drug without any problem. Examples of the biocompatible material include, but are not limited to, gelatin, agar, gum Arabic, polysaccharides, polyvinyl pyrrolidone, and polyethylene glycol. One of these biocompatible materials may be used alone or two or more of these biocompatible materials may be used in combination.

—Other Components—

The other components are not particularly limited and may be appropriately selected depending on the intended purpose. Examples of the other components include, but are not limited to, water, a taste masking agent, a fluidizer, an adsorbent, a lubricant, a flavoring agent, a surfactant, a fragrance, a colorant, an antioxidant, a masking agent, an antistatic agent, and a humectant. One of these other components may be used alone or two or more of these other components may be used in combination.

The taste masking agent is not particularly limited and may be appropriately selected depending on the intended purpose. Examples of the taste masking agent include, but are not limited to, L-menthol, sucrose, D-sorbitol, xylitol, citric acid, ascorbic acid, tartaric acid, malic acid, aspartame, acesulfame potassium, thaumatin, saccharin sodium, dipotassium glycyrrhizinate, sodium glutamate, sodium 5'-inosinate, and sodium 5'-guanylate. One of these taste masking agents may be used alone or two or more of these taste masking agents may be used in combination.

The fluidizer is not particularly limited and may be appropriately selected depending on the intended purpose. Examples of the fluidizer include, but are not limited to, light anhydrous silicic acid, hydrated silicon dioxide, and talc. One of these fluidizers may be used alone or two or more of these fluidizers may be used in combination.

Light anhydrous silicic acid may be a commercially available product. The commercially available product of light anhydrous silicic acid is not particularly limited and may be appropriately selected depending on the intended purpose. Examples of the commercially available product of light anhydrous silicic acid include, but are not limited to, ADSOLIDER 101 (available from Freund Corporation, with an average pore diameter of 21 nm).

The adsorbent may be a commercially available product. The commercially available product of the adsorbent is not particularly limited and may be appropriately selected depending on the intended purpose. Examples of the commercially available product of the adsorbent include, but are not limited to, product name: CARPLEX (component name: synthetic silica, a registered trademark of DSL Japan Co., Ltd.), product name: AEROSIL (a registered trademark of Nippon Aerosil Co., Ltd.) 200 (component name: hydrophilic fumed silica), product name: SYLICIA (component name: amorphous silicon dioxide, a registered trademark of Fuji Silysia Chemical Ltd.), and product name: ALCAMAC (component name: synthetic hydrotalcite, a registered trademark of Kyowa Chemical Industry Co., Ltd.). One of these adsorbents may be used alone or two or more of these adsorbents may be used in combination.

The lubricant is not particularly limited and may be appropriately selected depending on the intended purpose. Examples of the lubricant include, but are not limited to, magnesium stearate, calcium stearate, sucrose fatty acid ester, sodium stearyl fumarate, stearic acid, polyethylene glycol, and talc. One of these lubricants may be used alone or two or more of these lubricants may be used in combination.

The flavoring agent is not particularly limited and may be appropriately selected depending on the intended purpose. Examples of the flavoring agent include, but are not limited to, trehalose, malic acid, maltose, potassium gluconate, anise essential oil, vanilla essential oil, and cardamom essential oil. One of these flavoring agents may be used alone or two or more of these flavoring agents may be used in combination.

The surfactant is not particularly limited and may be appropriately selected depending on the intended purpose. Examples of the surfactant include, but are not limited to, polysorbates such as polysorbate 80; polyoxyethylene-polyoxypropylene copolymers; and sodium lauryl sulfate. One of these surfactants may be used alone or two or more of these surfactants may be used in combination.

The fragrance is not particularly limited and may be appropriately selected depending on the intended purpose. Examples of the fragrance include, but are not limited to, lemon oil, orange oil, and peppermint oil. One of these fragrances may be used alone or two or more of these fragrances may be used in combination.

The colorant is not particularly limited and may be appropriately selected depending on the intended purpose. Examples of the colorant include, but are not limited to, titanium oxide, Food Yellow No. 5, Food Blue No. 2, ferric oxide, and yellow ferric oxide. One of these colorants may be used alone or two or more of these colorants may be used in combination.

The antioxidant is not particularly limited and may be appropriately selected depending on the intended purpose. Examples of the antioxidant include, but are not limited to, sodium ascorbate, L-cysteine, sodium sulfite, and vitamin E. One of these antioxidants may be used alone or two or more of these antioxidants may be used in combination.

The masking agent is not particularly limited and may be appropriately selected depending on the intended purpose. Examples of the masking agent include, but are not limited to, titanium oxide. One of these masking agents may be used alone or two or more of these masking agents may be used in combination.

The antistatic agent is not particularly limited and may be appropriately selected depending on the intended purpose. Examples of the antistatic agent include, but are not limited to, talc and titanium oxide. One of these antistatic agents may be used alone or two or more of these antistatic agents may be used in combination.

The humectant is not particularly limited and may be appropriately selected depending on the intended purpose. Examples of the humectant include, but are not limited to, polysorbate 80, sodium lauryl sulfate, sucrose fatty acid ester, macrogol, and hydroxypropyl cellulose (HPC). One of these humectants may be used alone or two or more of these humectants may be used in combination.

The sheet of the present disclosure will be described in more detail with reference to the drawings.

Figure 1B:
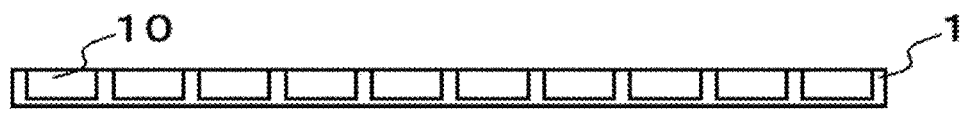
FIG. 1B is a side view of the base material of FIG. 1A seen from a side thereof.
Figure 19A:
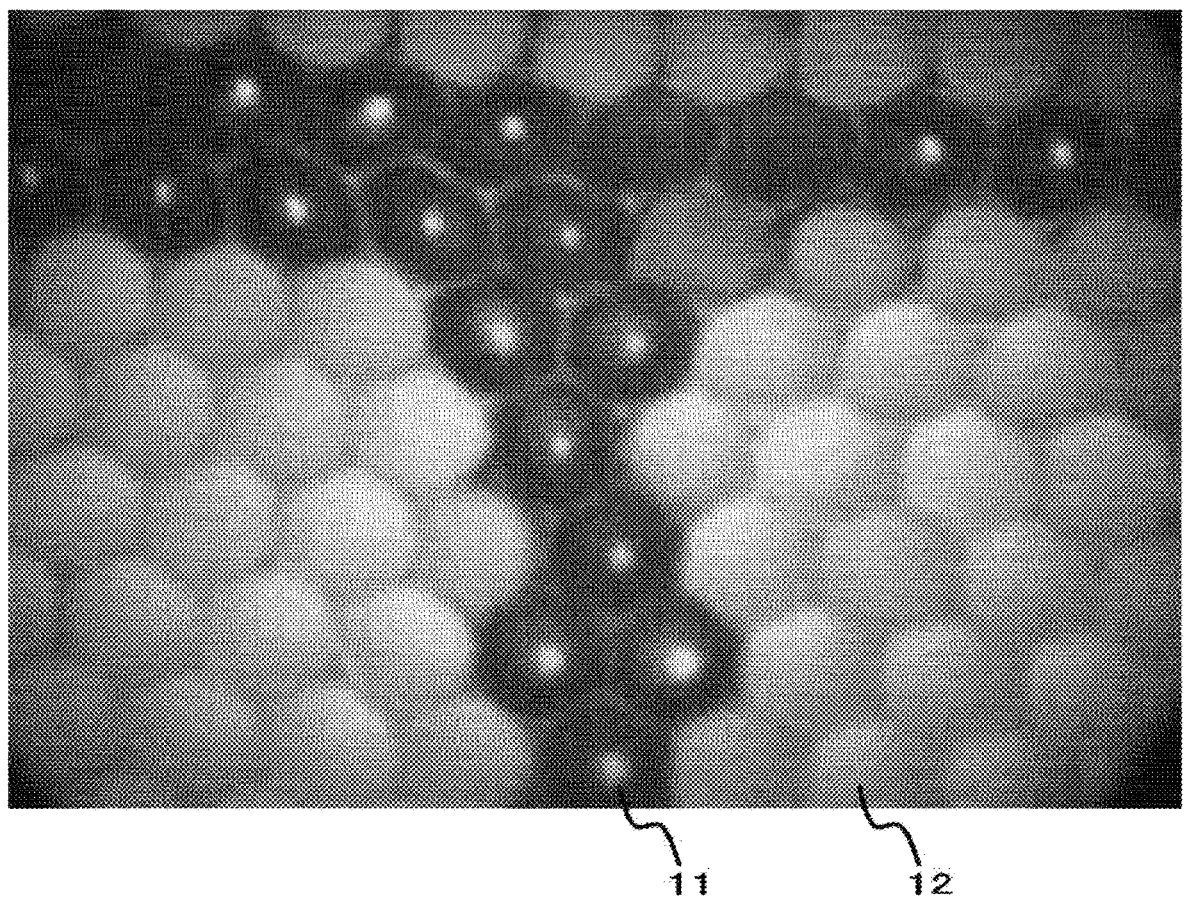
FIG. 19A is an example of a microscopic image of a sheet laminate according to an embodiment of the present disclosure captured from the top thereof.
Figure 19B:
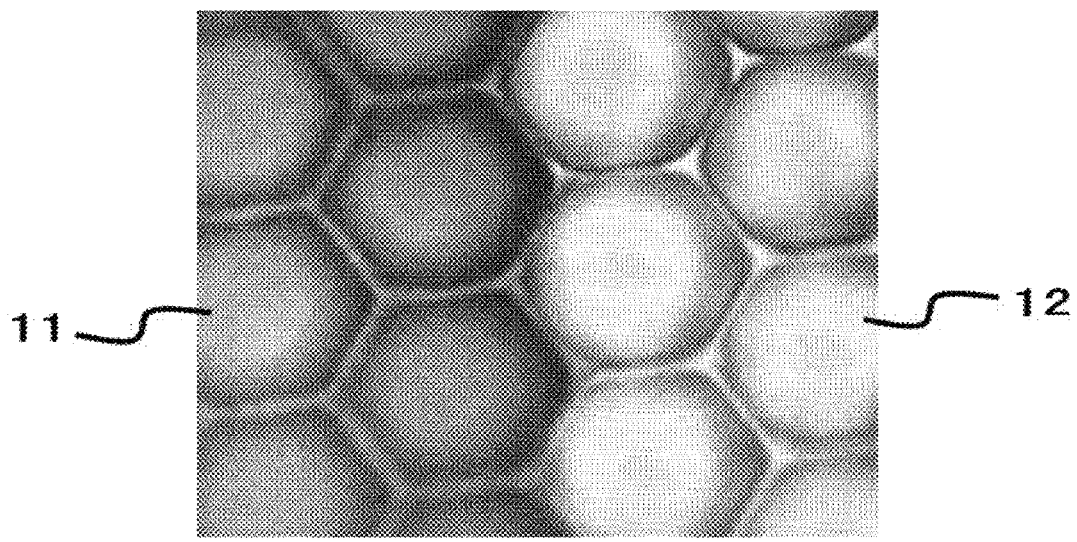
FIG. 19B is an example of a microscopic image of a sheet laminate according to an embodiment of the present disclosure captured from the top thereof.
Figure 19C:
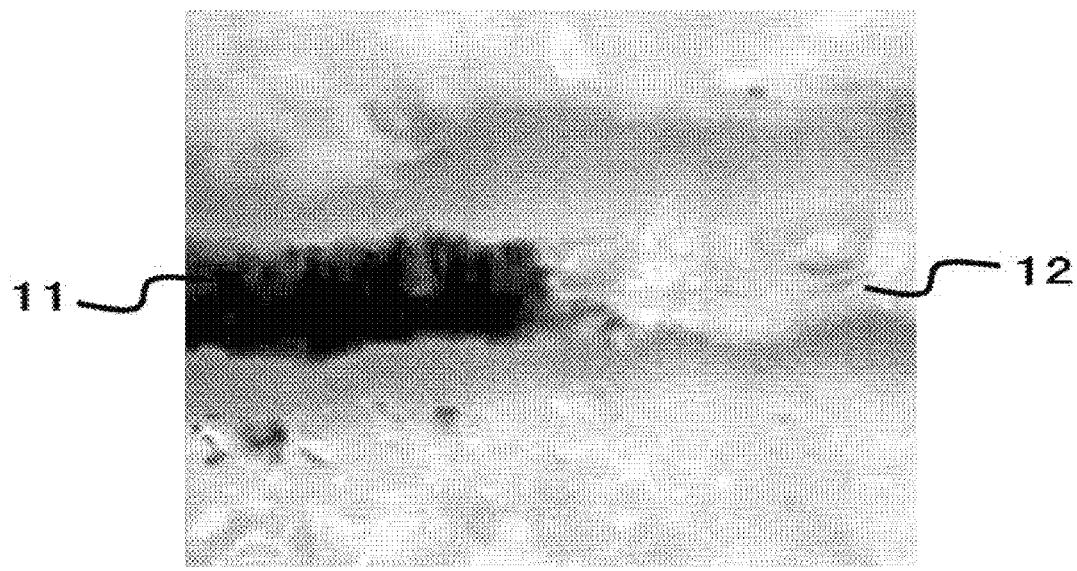
FIG. 19C is an example of a microscopic image of a sheet laminate according to an embodiment of the present disclosure captured from a side thereof.

FIG. 1A is a view illustrating an exemplary arrangement of the independent holes on the base material of the sheet of the present disclosure. FIG. 1B is a side view of the base material of FIG. 1A seen from a side thereof. FIG. 19A, FIG. 19B, and FIG. 19C are views illustrating examples of microscopic images of the sheet of the present disclosure. As illustrated in FIG. 1A and FIG. 1B, the sheet 1 of the present disclosure includes independent holes 10 which are completely independent of one another. FIG. 19A and FIG. 19B are views illustrating examples of microscopic images of the sheet laminate of the present disclosure captured from the top thereof. FIG. 19C is an example of a microscopic image of the sheet laminate of the present disclosure captured orthogonally to the direction of the thickness of the sheet laminate (i.e., captured from a side thereof). As illustrated in FIG. 19A to FIG. 19C, it can be seen that the substances contained in the independent holes A 11 are not mixed with each other and are clearly separated from adjacent independent holes B 12.

Figure 2:
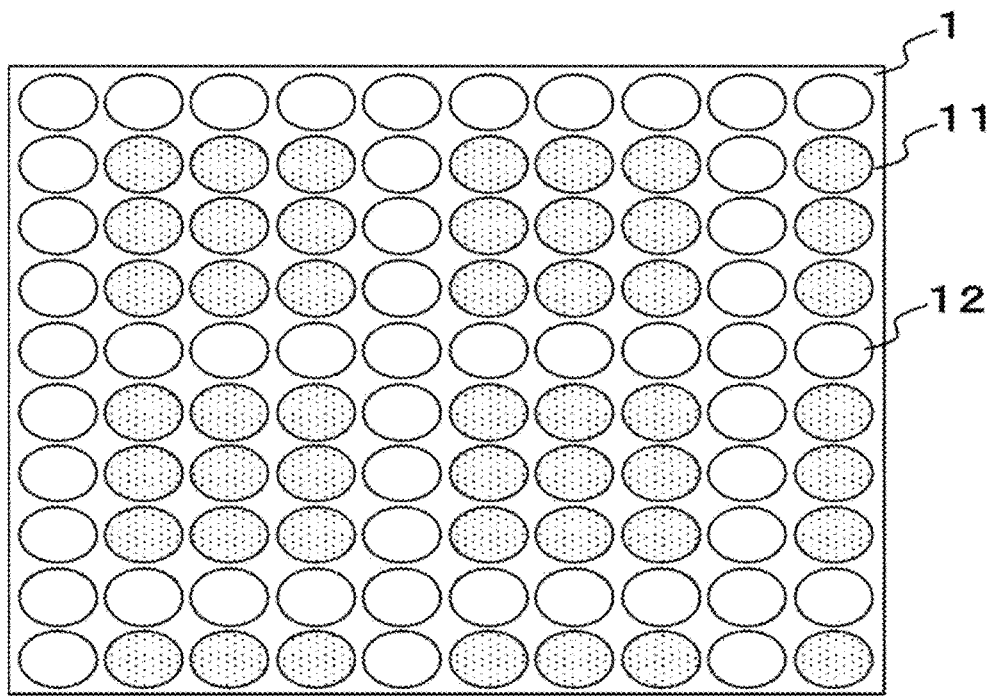
FIG. 2 is a view illustrating an example of a sheet according to an embodiment of the present disclosure.

FIG. 2 is a view illustrating an example of the sheet of the present disclosure. As illustrated in FIG. 2, the sheet 1 of the present disclosure includes independent holes A 11 containing bioactive substances and independent holes B 12 containing no bioactive substance. By arranging the independent holes A 11 and the independent holes B in a manner that the contour of a region having a predetermined shape formed of the plurality of adjacent independent holes A 11 is surrounded by the independent holes B 12, it is possible to cut out the region having the predetermined shape formed of the plurality of independent holes A 11 by cutting the sheet along the independent holes B 12, i.e., it is possible to form the sheet into a desired shape.

(Sheet Producing Method and Sheet Producing Apparatus)

A sheet producing method of the present disclosure is a method for producing the sheet of the present disclosure, includes an independent hole forming step of forming independent holes including at least one independent hole A and at least one independent hole B in a base material, and further includes other steps as needed.

A sheet producing apparatus of the present disclosure is an apparatus configured to produce the sheet of the present disclosure, includes an independent hole forming unit configured to form independent holes including at least one independent hole A and at least one independent hole B in a base material, and further includes other units as needed.

<Independent Hole Forming Step and Independent Hole Forming Unit>

The independent hole forming step is a step of forming independent holes including at least one independent hole A and at least one independent hole B in a base material, and can be suitably performed by the independent hole forming unit.

The method for forming independent holes in a base material in the independent hole forming step (means for forming independent holes) is not particularly limited and may be appropriately selected depending on the intended purpose. Examples of the method include, but are not limited to, a sheet forming method utilizing a gas pressure described in JP-4678731-B (corresponding to U.S. Pat. No. 8,617,335B) and JP-4869269-B (corresponding to U.S. Pat. No. 8,202,469B), and a fine hole drilling method. Of these methods, the fine hole drilling method is preferable. The fine hole drilling method can simplify the production process.

Examples of the fine hole drilling method include, but are not limited to, a method of opening holes in a base material by a desired number of times (number of holes) at desired positions of the base material by a punching blade having an arbitrary size (internal diameter) and an arbitrary shape.

The independent holes A are formed by containing bioactive substances in the independent holes formed in the base material.

The method for containing bioactive substances in the independent holes (means for forming independent holes) is not particularly limited and may be appropriately selected depending on the intended purpose. Examples of the method include, but are not limited to, an inkjet method and a dispenser method. Of these methods, the dispenser method is preferable. The dispenser method can inject a high amount per time and increase the productivity.

The bioactive substances used in the sheet producing method and the sheet producing apparatus are the same bioactive substances as used in the sheet of the present disclosure. Therefore, description about the bioactive substances is not given here.

The independent holes B are formed by containing no bioactive substances in the independent holes formed in the base material. That is, the independent holes B have a concave (hollow) structure filled with nothing but a substance other than the bioactive substances.

The substance other than the bioactive substances used in the sheet producing method and the sheet producing apparatus are the same substance as used in the sheet of the present disclosure is used. Therefore, description about the substance is not given here.

It is preferable that the independent hole forming step further include a step of forming independent holes C containing a thermoplastic material in addition to the independent holes A and the independent holes B.

The independent holes C are formed by containing a thermoplastic material in the independent holes formed in the base material.

The method for containing a thermoplastic material in the independent holes (means for forming independent holes) is not particularly limited and may be appropriately selected depending on the intended purpose. The same method as used for forming the independent holes A can be used.

<Other Steps and Other Units>

The other steps and the other units are not particularly limited and may be appropriately selected depending on the intended purpose. Examples of the other steps and the other units include, but are not limited to, a shaping step and a shaping unit.

The shaping step is a step of forming the sheet into a predetermined shape, and can be suitably performed by the shaping unit.

The shaping unit is not particularly limited and may be appropriately selected depending on the intended purpose. Examples of the shaping unit include, but are not limited to, a punching device having a punching blade conforming to a predetermined shape.

(Sheet Laminate)

A sheet laminate of the present disclosure includes sheets laminated with each other, each of the sheets being the sheet of the present disclosure.

The sheet laminate of the present disclosure is obtained by laminating a sheet including a base material having at least two independent holes, wherein at least one of the independent holes is an independent hole A containing a bioactive substance and at least one of the independent holes is an independent hole B containing no bioactive substance, wherein the base material contains a biocompatible material. The sheet laminate further includes other members as needed.

<Base Material>

The base material may be the same as the base material used in the sheet of the present disclosure. Therefore, description about the base material is not given here.

<Other Members>

The other members are not particularly limited and may be appropriately selected depending on the intended purpose. Examples of the other members include, but are not limited to, an adhesive layer.

The adhesive layer is a layer provided between a sheet and another sheet and containing at least any one selected from biocompatible materials and thermoplastic materials.

With the adhesive layer provided in the sheet laminate, the mechanical strength of the sheet laminate can be increased and the sheet laminate can be prevented from breakage during transportation.

With the material of the adhesive layer containing at least any one selected from biocompatible materials and thermoplastic materials, the adhesive layer has an increased affinity with the sheet contacted by the adhesive layer. Therefore, the mechanical strength can be increased. The biocompatible material and the thermoplastic material may be the same as the biocompatible material and the thermoplastic material that can be used in the sheet of the present disclosure. Therefore, description about the biocompatible material and the thermoplastic material is not given here.

(Sheet Laminate Producing Method and Sheet Laminate Producing Apparatus)

A sheet laminate producing method of the present disclosure is a method for producing the sheet laminate of the present disclosure, includes an independent hole forming step of forming independent holes including at least one independent hole A and at least one independent hole B and a laminating step of laminating sheets, and further includes other steps as needed.

A sheet laminate producing apparatus of the present disclosure is an apparatus configured to produce the sheet laminate of the present disclosure, includes an independent hole forming unit configured to form independent holes including at least one independent hole A and at least one independent hole B and a laminating unit configured to laminate sheets, and further includes other units as needed.

<Independent Hole Forming Step and Independent Hole Forming Unit>

The independent hole forming step and the independent hole forming unit may be the same as the step and the unit in the sheet producing method and the sheet producing apparatus of the present disclosure. Therefore, description about the independent hole forming step and the independent hole forming unit is not given here.

<Laminating Step and Laminating Unit>

The laminating step is a step of laminating sheets produced, and is suitably performed by the laminating unit.

The laminating step is a step of overlapping one sheet produced with another sheet produced, and crimping the contacting portions of the sheets.

The laminating unit is not particularly limited and may be appropriately selected depending on the intended purpose. Examples of the laminating unit include, but are not limited to, a unit configured to convey and overlap one sheet produced with another sheet produced and crimp the contacting portions of the sheets, and a unit configured to provide an adhesive layer over one sheet produced. The material of the adhesive layer is not particularly limited and may be appropriately selected depending on the intended purpose. Examples of the material include, but are not limited to, polyethylene glycol (PEG), gelatin, agar, polylactic acid (PLA), and polyvinyl pyrrolidone (PVP).

<Other Steps and Other Units>

The other steps and the other units may be the same as the steps and the units in the sheet producing method and the sheet producing apparatus of the present disclosure. Therefore, description about the other steps and the other units is not given here.

(Pharmaceutical Drug)

A pharmaceutical drug of the present disclosure contains at least any one of the sheet of the present disclosure and the sheet laminate of the present disclosure, and further contains a dispersant, additives, and other components as needed.

The dosage form of the pharmaceutical drug of the present disclosure may be appropriately selected depending on the intended purpose. Examples of the dosage form include, but are not limited to, tablet, peptizer, drop, lozenge, film preparation, capsule, suppository, intercalating agent, and patch.

EXAMPLES

Figure 3A:
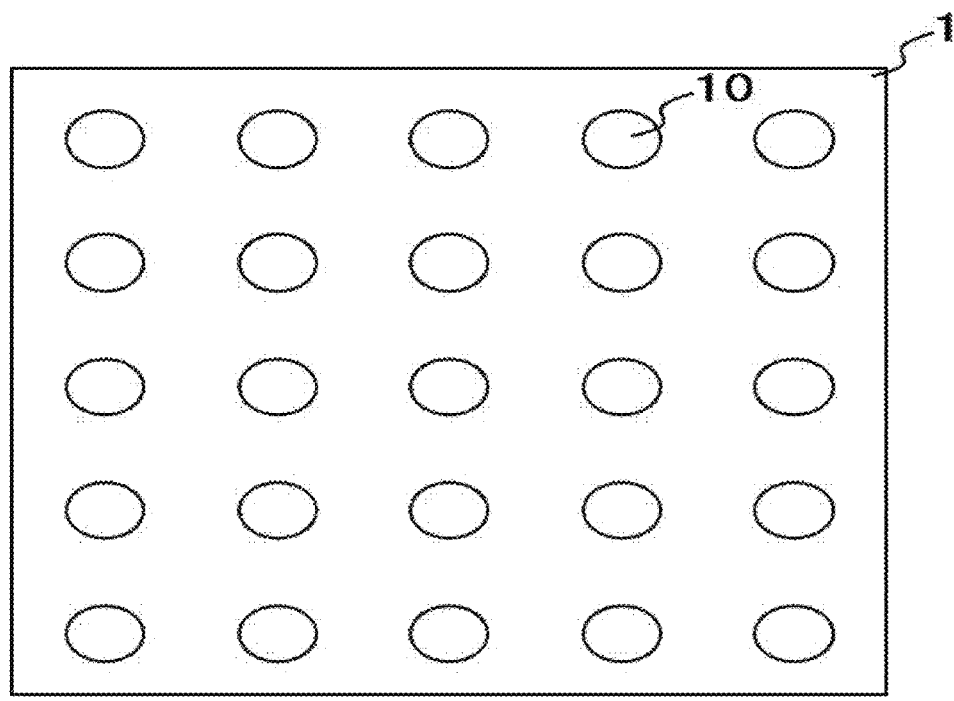
FIG. 3A is a view illustrating another exemplary arrangement of independent holes in a base material of a sheet according to an embodiment of the present disclosure.
Figure 3B:
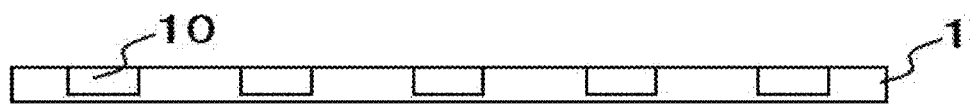
FIG. 3B is a side view of the base material of FIG. 3A seen from a side thereof.
Figure 4:
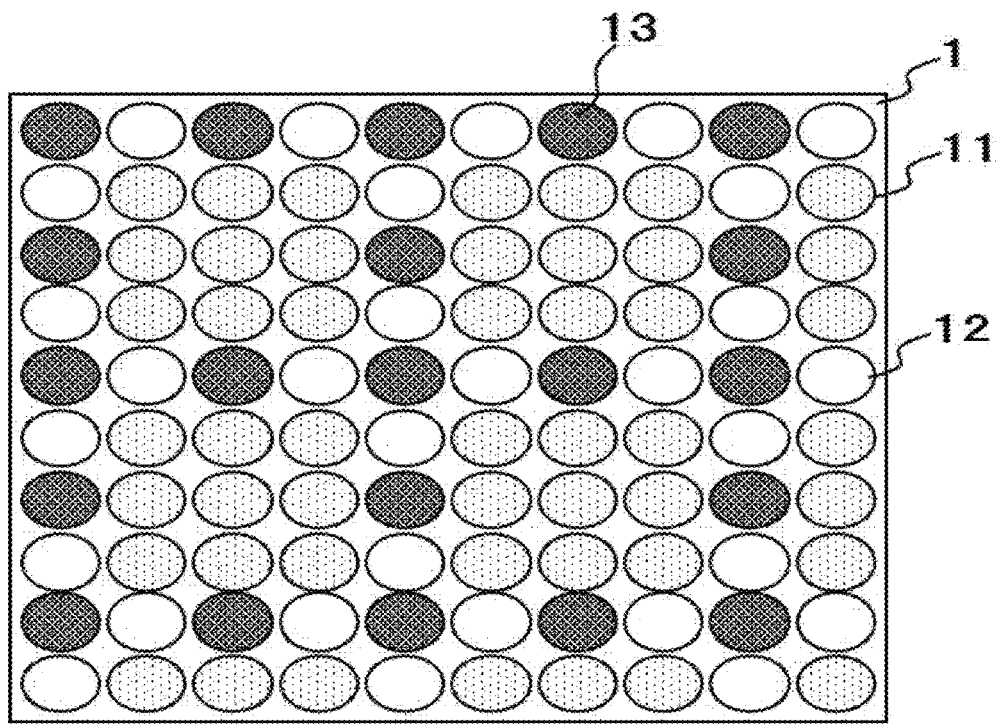
FIG. 4 is a view illustrating another example of a sheet according to an embodiment of the present disclosure.

The present disclosure will be described below by way of Examples. The present disclosure should not be construed as being limited to these Examples.
—Production of Base Material—
<Production of Base Material 1>
To gelatin (available from Kanto Corporation, product name:RM-GELATIN RM-100) as a biocompatible material, glycerin (available from Taiyo Pharmaceutical Co., Ltd.) as an additive was added in an amount of 20% by mass together with distilled water (available from Kyoei Pharmaceutical Co., Ltd.), to prepare a 30% by mass gelatin aqueous solution. This gelatin aqueous solution was coated over a polycarbonate film with a die coater set to a clearance of 2 mm, and subsequently dried with a fixed-temperature drier (available from AS ONE Corporation, apparatus name: OFW-300S) at 80 degrees C. for 8 hours, to obtain a base material (a single-layer sheet). This base material was repeatedly pierced with a 30 G needle (with a circular hole shape and a diameter of 0.12 mm±0.03 mm) in a manner that the shortest distance between the centers of adjacent holes would be 0.1 mm, to produce a base material 1 having an opening ratio of 50% (opening ratio: a ratio of the area of openings in the surface of the base material including the openings of the holes) (fine hole drilling method). The base material 1 is illustrated in FIG. 1A.
<Production of Base Material 2>
A base material 2 was produced in the same manner as in Production of base material 1, except that unlike in Production of base material 1, the shortest distance between the centers of adjacent holes was set to 0.2 mm, to obtain an opening ratio of 28%. The base material 2 is illustrated in FIG. 3A and FIG. 3B.
<Production of Sheet>
—Sheet Production Example A1—
A 10% by mass vitamin B water dispersion liquid was prepared using vitamin B2 (available from Nacalai Tesque Inc.). The 10% by mass vitamin B water dispersion liquid was discharged into the independent holes 10 of the produced base material 1 in the arrangement illustrated in FIG. 2 with a dispenser (available from Musashi Engineering, Inc., product name: SUPER ΣxIII), to form independent holes A (each denoted by 11 in FIG. 2) containing a bioactive substance and independent holes B (each denoted by 12 in FIG. 2) which were hollow concaves. After the independent holes were formed, the resultant was dried at 40 degrees C. for 120 minutes. With a die coater set to a clearance of 100 micrometers, the surface including the openings of the independent holes was coated with polyethylene glycol (PEG) 2000 (available from FUJIFILM Wako Pure Chemical Corporation) heated and melted at 60 degrees C., to produce a sheet A1.
—Sheet Production Example A2—
A sheet A2 was produced in the same manner as in Sheet production example A1, except that unlike in Sheet production example A1, independent holes C (each denoted by 13 in FIG. 4) containing a thermoplastic material were formed in the produced base material 1 in the arrangement illustrated in FIG. 4 by using a dispenser (available from Musashi Engineering, Inc., product name: SUPER ΣxIII) to discharge polyethylene glycol 2000 (PEG2000) heated and melted at 60 degrees C., in addition to independent holes A (each denoted by 11 in FIG. 4) and independent holes B (each denoted by 12 in FIG. 4).
—Sheet Production Example A3—
A sheet A3 was produced in the same manner as in Sheet production example A2, except that unlike in Sheet production example A2, independent holes $A_2$ (each denoted by 112 in FIG. 5) containing a 10% by mass vitamin K water dispersion liquid were formed in the arrangement illustrated in FIG. 5 in addition to independent holes $A_1$ (each denoted by 111 in FIG. 5) containing a 10% by mass vitamin B water dispersion liquid.
—Sheet Production Example A4—
A sheet A4 was produced in the same manner as in Sheet production example A3, except that unlike in Sheet production example A3, the number of independent holes A was set to 70, the number of independent holes B was set to 5, and the number of independent holes C was set to 25 in the arrangement illustrated in FIG. 6.
—Sheet Production Example A5—
A sheet A5 was produced in the same manner as in Sheet production example A3, except that unlike in Sheet production example A3, the number of independent holes A was set to 70, the number of independent holes B was set to 25, and the number of independent holes C was set to 5 in the arrangement illustrated in FIG. 7.
—Sheet Production Example A6—
A sheet A6 was produced in the same manner as in Sheet production example A3, except that unlike in Sheet production example A3, the number of independent holes A was set to 5, the number of independent holes B was set to 45, and the number of independent holes C was set to 50 in the arrangement illustrated in FIG. 8.
—Sheet Production Example A7—
A sheet A7 was produced in the same manner as in Sheet production example A3, except that unlike in Sheet production example A3, the number of independent holes A was set to 2, the number of independent holes B was set to 9, and the number of independent holes C was set to 89 in the arrangement illustrated in FIG. 9.
—Sheet Production Example A8—
A sheet A8 was produced in the same manner as in Sheet production example A3, except that unlike in Sheet production example A3, the number of independent holes A was set to 2, the number of independent holes B was set to 89, and the number of independent holes C was set to 9 in the arrangement illustrated in FIG. 10.
—Sheet Production Example A9—
A sheet A9 was produced in the same manner as in Sheet production example A3, except that unlike in Sheet production example A3, the number of independent holes A was set to 92, the number of independent holes B was set to 4, and the number of independent holes C was set to 4 in the arrangement illustrated in FIG. 11.
—Sheet Production Example A10—
A sheet A10 was produced in the same manner as in Sheet production example A3, except that unlike in Sheet production example A3, the number of independent holes A was set to 2, the number of independent holes B was set to 3, and the number of independent holes C was set to 95 in the arrangement illustrated in FIG. 12.
—Sheet Production Example A11—
A sheet A11 was produced in the same manner as in Sheet production example A3, except that unlike in Sheet production example A3, the number of independent holes A was set to 2, the number of independent holes B was set to 95, and the number of independent holes C was set to 3 in the arrangement illustrated in FIG. 13.

—Sheet Production Example A12—

Figure 14:
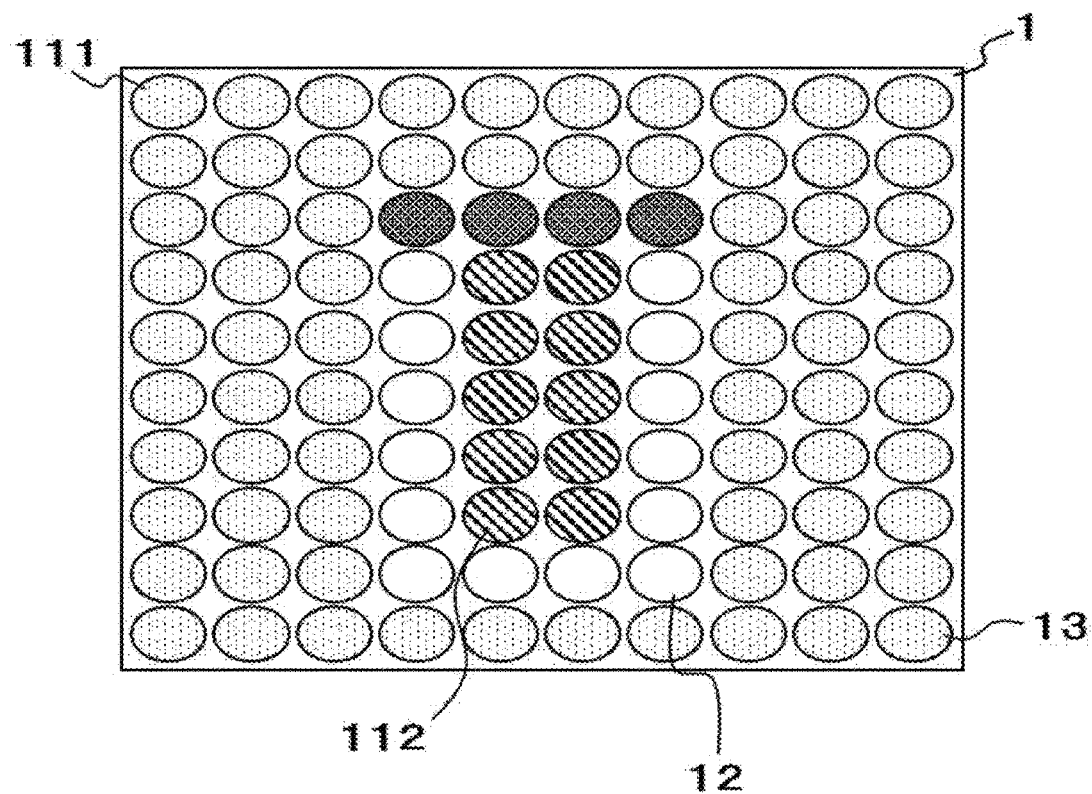
FIG. 14 is a view illustrating another example of a sheet according to an embodiment of the present disclosure.

A sheet A12 was produced in the same manner as in Sheet production example A3, except that unlike in Sheet production example A3, the number of independent holes A was set to 82, the number of independent holes B was set to 14, and the number of independent holes C was set to 4 in the arrangement illustrated in FIG. 14.

—Sheet Production Example A13—

Figure 15:
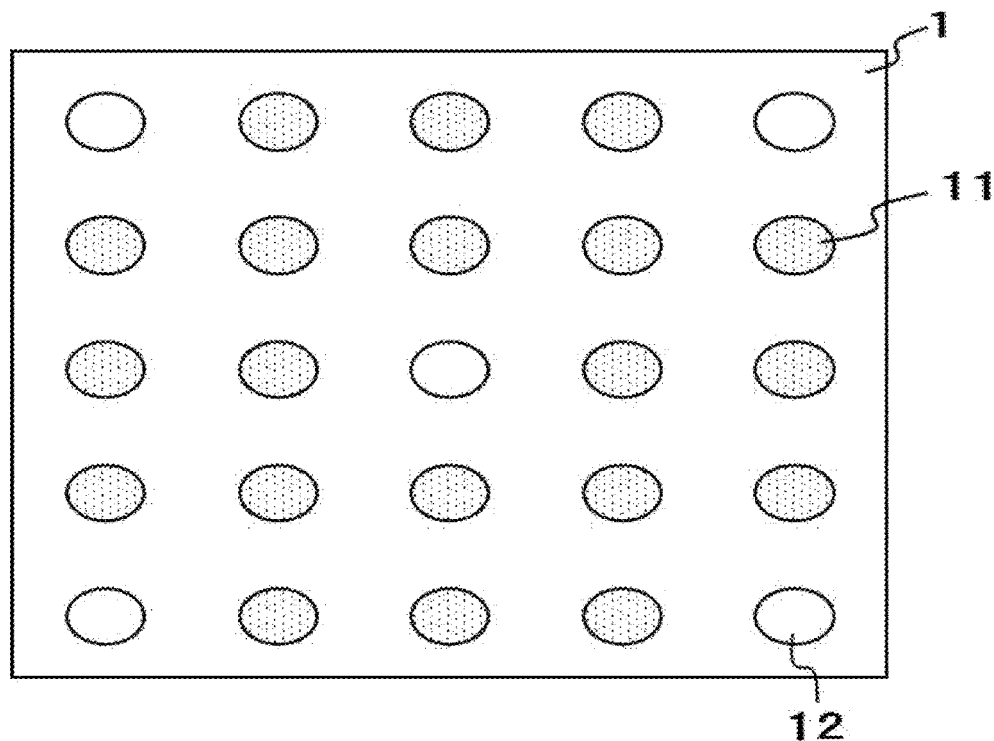
FIG. 15 is a view illustrating another example of a sheet according to an embodiment of the present disclosure.

A 10% by mass vitamin B water dispersion liquid was prepared using vitamin B2 (available from Nacalai Tesque Inc.). The 10% by mass vitamin B water dispersion liquid was discharged into the independent holes 10 of the produced base material 2 in the arrangement illustrated in FIG. 15 with a dispenser (available from Musashi Engineering, Inc., product name: SUPER ΣxIII), to form independent holes A containing a bioactive substance and independent holes B which were hollow concaves. After the independent holes were formed, the resultant was dried at 40 degrees C. for 120 minutes. With a die coater set to a clearance of 100 micrometers, the surface including the openings of the independent holes was coated with polyethylene glycol 2000 (available from FUJIFILM Wako Pure Chemical Corporation) heated and melted at 60 degrees C., to produce a sheet A13.

—Sheet Production Example A14—

Figure 16:
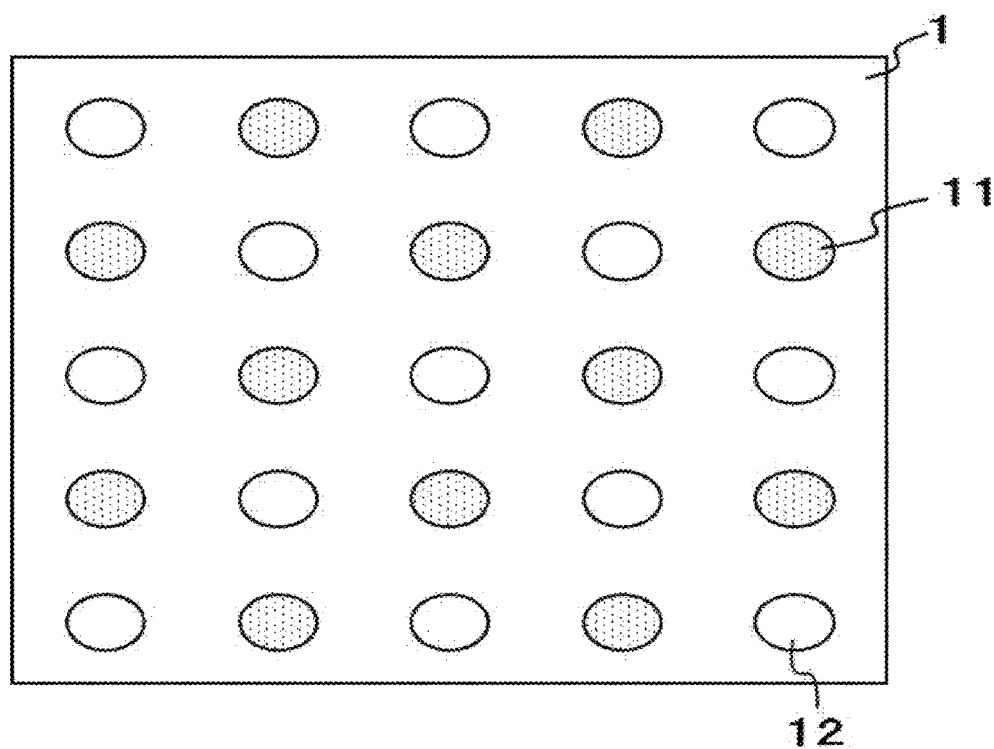
FIG. 16 is a view illustrating another example of a sheet according to an embodiment of the present disclosure.

A sheet A14 was produced in the same manner as in Sheet production example A13, except that unlike in Sheet production example A13, the independent holes A and the independent holes B were arranged in the arrangement illustrated in FIG. 16.

—Sheet Production Example A15—

A sheet A15 was produced in the same manner as in Sheet production example A1, except that unlike in Sheet production example A1, the 10% by mass vitamin B water dispersion liquid was discharged to and contained in all independent holes.

The configurations of the sheets A1 to A15 produced in Sheet production examples A1 to A15 are presented in Table 1.

TABLE 1

| | Sheet No. | Base material Biocompatible material | Additive (glycerin) (% by mass) | Independent holes A $A_1$ Material contained | $A_2$ Material contained | Ratio of number of holes A (%) |
|---|---|---|---|---|---|---|
| Production ex. | A1 | Gelatin | 20 | Vitamin B | — | 49 |
| | A2 | Gelatin | 20 | Vitamin B | — | 49 |
| | A3 | Gelatin | 20 | Vitamin B | Vitamin K | 49 |
| | A4 | Gelatin | 20 | Vitamin B | Vitamin K | 70 |
| | A5 | Gelatin | 20 | Vitamin B | Vitamin K | 70 |
| | A6 | Gelatin | 20 | Vitamin B | Vitamin K | 5 |
| | A7 | Gelatin | 20 | Vitamin B | Vitamin K | 2 |
| | A8 | Gelatin | 20 | Vitamin B | Vitamin K | 2 |
| | A9 | Gelatin | 20 | Vitamin B | Vitamin K | 92 |
| | A10 | Gelatin | 20 | Vitamin B | Vitamin K | 2 |
| | A11 | Gelatin | 20 | Vitamin B | Vitamin K | 2 |
| | A12 | Gelatin | 20 | Vitamin B | Vitamin K | 82 |
| | A13 | Gelatin | 20 | Vitamin B | Vitamin K | 80 |
| | A14 | Gelatin | 20 | Vitamin B | Vitamin K | 48 |
| | A15 | Gelatin | 20 | Vitamin B | — | 100 |

| | Sheet No. | Independent holes B Material contained | Ratio of number of holes B (%) | Independent holes C Material contained | Ratio of number of holes C (%) | Sum of ratios of numbers of holes B and holes C (%) |
|---|---|---|---|---|---|---|
| Production ex. | A1 | Hollow | 51 | — | — | 51 |
| | A2 | Hollow | 27 | PEG2000 | 24 | 51 |
| | A3 | Hollow | 27 | PEG2000 | 24 | 51 |
| | A4 | Hollow | 5 | PEG2000 | 25 | 30 |
| | A5 | Hollow | 25 | PEG2000 | 5 | 30 |
| | A6 | Hollow | 45 | PEG2000 | 50 | 95 |
| | A7 | Hollow | 9 | PEG2000 | 89 | 98 |
| | A8 | Hollow | 89 | PEG2000 | 9 | 98 |
| | A9 | Hollow | 4 | PEG2000 | 4 | 8 |
| | A10 | Hollow | 3 | PEG2000 | 95 | 98 |
| | A11 | Hollow | 95 | PEG2000 | 3 | 98 |
| | A12 | Hollow | 14 | PEG2000 | 4 | 18 |
| | A13 | Hollow | 20 | — | — | 20 |
| | A14 | Hollow | 52 | — | — | 52 |
| | A15 | — | — | — | — | — |

Next, the sheets obtained in Production examples A1 to A15 were measured and evaluated in the manners described in "evaluation of water disintegrability", "evaluation of elution of bioactive substance", "evaluation of mechanical strength", and "evaluation of transportation durability" below. The results are presented in Table 2.

<Evaluation of Water Disintegrability>

A stirring bar having a size of 18 mm×6 mm (in diameter) and pure water (100 mL) were put in a 200 mL tall beaker (available from Iwaki & Co., Ltd.), to stir the pure water at a rotation speed of 200 rpm. A sample obtained by forming the sheet into a circle having a diameter of 10 mm was put in a hemispherical bowl-shaped container having a radius of 20 mm and a hook. The bowl-shaped container had been formed by machining 18 mesh stainless steel having a wire diameter of 0.5 mm. The bowl-shaped container having a hook was hooked on the 200 mL tall beaker, to immerse the sample in the water. The thickness of the sample was arbitrary. In the case of a sheet, seeing a timing at which the sample was entirely immersed as 0 seconds, the time taken afterwards for the sheet to be visually observed to break into three or more pieces was obtained as a measurement. The test was conducted three times, to calculate the average as a disintegration time and evaluate the disintegration time according to the evaluation criteria described below.

[Evaluation Criteria]

10 points: Shorter than 10 seconds 8 points: 10 seconds or longer but shorter than 60 seconds 6 points: 60 seconds or longer but shorter than 180 seconds 4 points: 180 seconds or longer but shorter than 300 seconds 2 points: 300 seconds or longer but shorter than 900 seconds 0 points: 900 seconds or longer <Evaluation of Elution of Bioactive Substance>

A stirring bar having a size of 18 mm×6 mm (in diameter) and pure water (100 mL) were put in a 200 mL tall beaker (available from Iwaki & Co., Ltd.), to stir the pure water at a rotation speed of 200 rpm. A sample obtained by forming the sheet into a circle having a diameter of 10 mm was put in a hemispherical bowl-shaped container having a radius of 20 mm and a hook. The bowl-shaped container had been formed by machining 18 mesh stainless steel having a wire diameter of 0.5 mm. The bowl-shaped container having a hook was hooked on the 200 mL tall beaker, to immerse the sample in the water. The thickness of the sample was arbitrary. Seeing a timing at which the sample was entirely immersed as 0 seconds, the refractive index of the liquid in the beaker after 60 minutes was measured, to calculate the concentration as a measurement and measure the elution rate according to the formula described below. The test was conducted three times, to evaluate the average elution rate according to the evaluation criteria described below.

$$\text{Elution rate} = (\text{measurement})/(\text{theoretical concentration when the sample had completely eluted}) \times 100 \quad \text{Formula 1}$$

[Evaluation Criteria]

10 points: 90% or higher but 100% or lower 0 points: Lower than 90%

<Mechanical Strength Testing>

The breaking strength of the sheet formed into a circle having a diameter of 10 mm was measured with a tablet hardness tester (product name: TH-1, available from AS ONE Corporation). The thickness of the sheet was arbitrary. The strength of the sheet was measured at a breaking point, which was a timing at which visually observable cracking or chipping occurred in the sheet. The test was conducted three times, and the average value of strength was divided by the thickness, to obtain a breaking strength. The breaking strength was evaluated according to the evaluation criteria described below.

[Evaluation Criteria]

10 points: 0.5 kg/mm or greater 5 points: 0.14 kg/mm or greater but less than 0.5 kg/mm 2 points: 0.05 kg/mm or greater but less than 0.14 kg/mm 0 points: Less than 0.05 kg/mm <Transportation Durability Testing>

A dropping device used was formed of an acrylic pipe having a length of 1.0 m and an internal diameter of 10 cm and an acrylic plate coupled to one end of the acrylic pipe in a manner that the surface of the acrylic plate was orthogonal to the longer-axis direction of the pipe. The end of the dropping device having the acrylic plate was placed on a horizontal table. The sheet formed into a circle having a diameter of 10 mm was let to freely fall from the open end of the pipe, to visually observe how the landed sheet would be damaged. The test was conducted ten times, and evaluation was performed according to the evaluation criteria described below, to obtain the average as the test result.

[Evaluation Criteria]

The number of times the landed sheet had chipped or cracked by 1 mm or greater in the ten times of evaluation was evaluated according to the evaluation criteria described below.

10 times: 0 points 9 times: 1 point 8 times: 2 points 7 times: 3 points 6 times: 4 points 5 times: 5 points 4 times: 6 points 3 times: 7 points 2 times: 8 points 1 time: 9 points 0 times: 10 points <Total Evaluation>

The total of the points in each evaluation described above was evaluated according to the evaluation criteria described below.

[Evaluation Criteria]

A: 36 points or greater but 40 points or less

B: 31 points or greater but 35 points or less

C: 26 points or greater but 30 points or less

D: 21 points or greater but 25 points or less

E: 16 points or greater but 20 points or less

F: 15 points or less

TABLE 2

| | | Sheet No. | Thickness (mm) | Evaluation of water disintegrability | | Evaluation of elution | |
|---|---|---|---|---|---|---|---|
| | | | | Disintegration time (second) | Evaluation | Average elution rate (%) | Evaluation |
| Ex. | 1 | A1 | 0.8 | 171 | 6 | 95 | 10 |
| | 2 | A2 | 0.8 | 250 | 4 | 93 | 10 |
| | 3 | A3 | 0.8 | 260 | 4 | 93 | 10 |
| | 4 | A4 | 0.8 | 450 | 2 | 92 | 10 |
| | 5 | A5 | 0.8 | 213 | 4 | 95 | 10 |
| | 6 | A6 | 0.8 | 152 | 6 | 95 | 10 |
| | 7 | A7 | 0.8 | 266 | 4 | 95 | 10 |
| | 8 | A8 | 0.8 | 123 | 6 | 95 | 10 |
| | 9 | A9 | 0.8 | 678 | 2 | 92 | 10 |
| | 10 | A10 | 0.8 | 258 | 4 | 94 | 10 |
| | 11 | A11 | 0.8 | 59 | 8 | 99 | 10 |
| | 12 | A12 | 0.8 | 268 | 4 | 94 | 10 |
| | 13 | A13 | 0.8 | 294 | 4 | 92 | 10 |
| | 14 | A14 | 0.8 | 276 | 4 | 93 | 10 |
| Comp. Ex. 1 | | A15 | 0.8 | 1,034 | 0 | 73 | 0 |

| | | Evaluation of mechanical strength | | Evaluation of transportation durability | | Total evaluation | |
|---|---|---|---|---|---|---|---|
| | | Breaking strength (kg/mm) | Evaluation | Number of samples chipped | Evaluation | Total | |
| Ex. | 1 | 0.20 | 5 | 0 | 10 | 31 | B |
| | 2 | 0.30 | 5 | 0 | 10 | 29 | C |
| | 3 | 0.30 | 5 | 0 | 10 | 29 | C |
| | 4 | 0.40 | 5 | 0 | 10 | 27 | C |
| | 5 | 0.20 | 5 | 1 | 9 | 28 | C |
| | 6 | 0.30 | 5 | 0 | 10 | 31 | B |
| | 7 | 0.20 | 5 | 0 | 10 | 29 | C |
| | 8 | 0.20 | 5 | 1 | 9 | 30 | C |
| | 9 | 0.10 | 2 | 0 | 10 | 24 | D |
| | 10 | 0.20 | 5 | 0 | 10 | 29 | C |
| | 11 | 0.10 | 2 | 1 | 9 | 29 | C |
| | 12 | 0.10 | 2 | 0 | 10 | 26 | C |
| | 13 | 0.08 | 2 | 0 | 10 | 26 | C |
| | 14 | 0.07 | 2 | 0 | 10 | 26 | C |
| Comp. Ex. 1 | | 0.4 | 5 | 3 | 7 | 12 | F |

<Production of Sheet Laminate>

—Sheet Laminate Production Example B1—

Figure 17A:
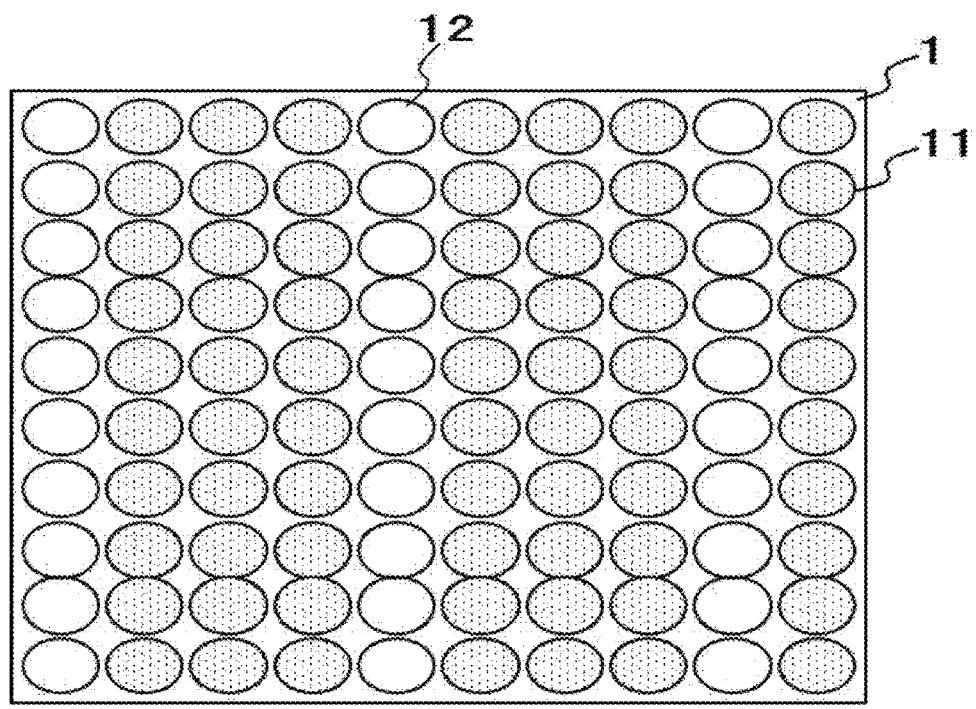
FIG. 17A is a view illustrating an example of a sheet laminate according to an embodiment of the present disclosure.
Figure 17B:
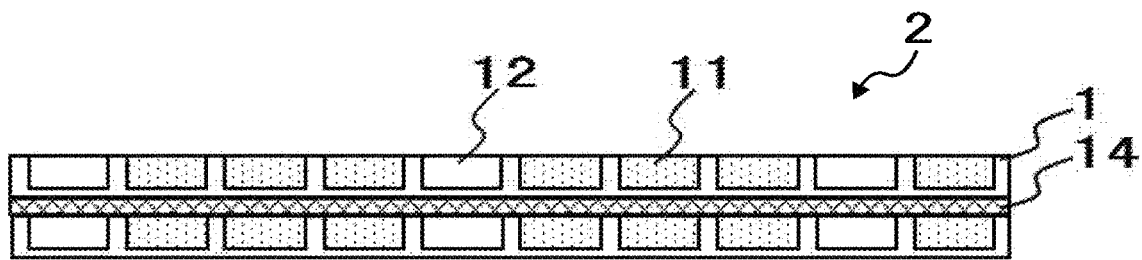
FIG. 17B is a side view illustrating the sheet laminate of FIG. 17A seen from a side thereof.

A base material was produced in the same manner as in Production of base material 1 except that unlike in Production of base material 1, a gelatin aqueous solution was coated over a polycarbonate film with a die coater set to a clearance of 1 mm. A 10% by mass vitamin B water dispersion liquid was prepared using vitamin B2 (available from Nacalai Tesque Inc.). The 10% by mass vitamin B water dispersion liquid was discharged into the independent holes of the base material in the arrangement illustrated in FIG. 17A with a dispenser (available from Musashi Engineering, Inc., product name: SUPER ΣxIII), to form independent holes A (each denoted by 11 in FIG. 17A) containing a bioactive substance and independent holes B (each denoted by 12 in FIG. 17A) which were hollow concaves. After the independent holes were formed, the resultant was dried at 40 degrees C. for 120 minutes. With a die coater set to a clearance of 100 micrometers, the surface including the openings of the independent holes was coated with polyethylene glycol 2000 (PEG2000) (available from FUJIFILM Wako Pure Chemical Corporation) heated and melted at 60 degrees C. as an adhesive layer 14 (illustrated in FIG. 17B). Another sheet produced in the same manner was overlapped with the adhesive layer, and the sheets were crimped, to produce a sheet laminate B1 (denoted by 2 in FIG. 17B).

—Sheet Laminate Production Example B2—

Figure 18:
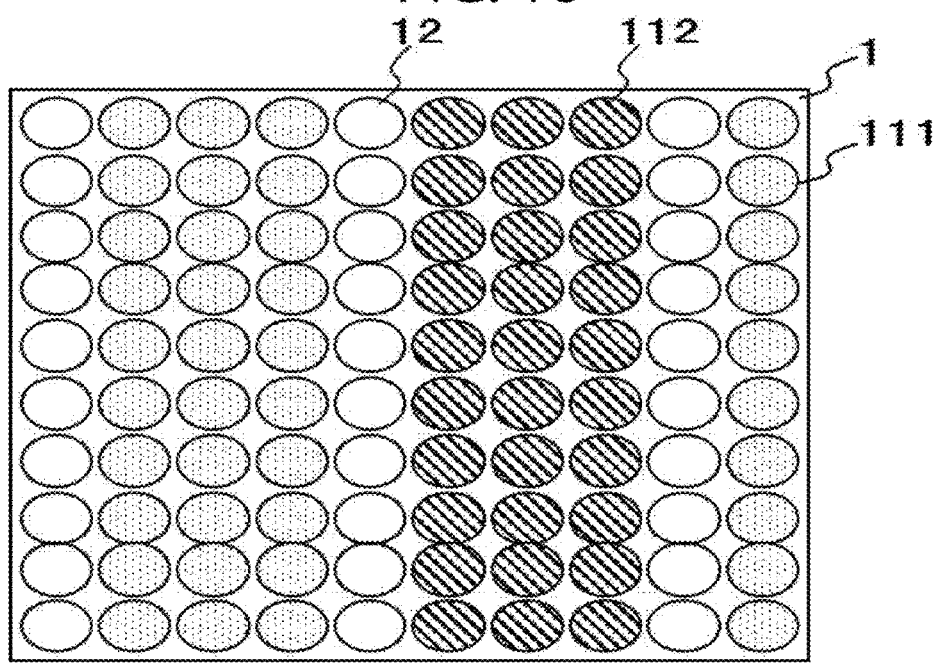
FIG. 18 is a view illustrating another example of a sheet laminate according to an embodiment of the present disclosure.

A sheet laminate B2 was produced in the same manner as in Sheet laminate production example B1, except that unlike in Sheet laminate production example B1, independent holes $A_2$ (each denoted by 112 in FIG. 18) containing a 10% by mass vitamin K water dispersion liquid were formed in the arrangement illustrated in FIG. 18 in addition to independent holes $A_1$ (each denoted by 111 in FIG. 18) containing a 10% by mass vitamin B water dispersion liquid, and the adhesive layer 14 was changed to gelatin (available from Kanto Chemical Co., Inc., product name: RM-GELATIN RM-100).

—Sheet Laminate Production Example B3—

Figure 5:
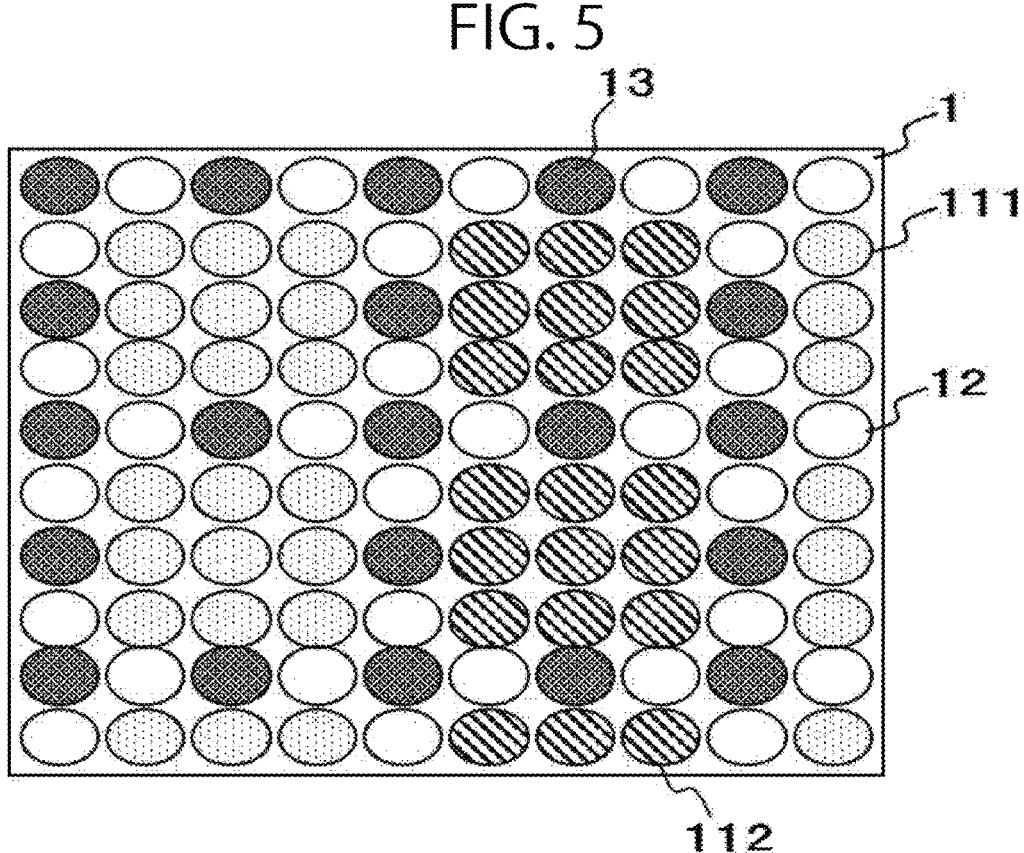
FIG. 5 is a view illustrating another example of a sheet according to an embodiment of the present disclosure.

A sheet laminate B3 was produced in the same manner as in Sheet laminate production example B1, except that unlike in Sheet laminate production example B1, independent holes $A_2$ (each denoted by 112 in FIG. 5) containing a 10% by mass vitamin K water dispersion liquid, and independent holes C (each denoted by 13 in FIG. 5) containing a thermoplastic material were formed in the arrangement illustrated in FIG. 5, in addition to independent holes $A_1$ (each denoted by 111 in FIG. 5) containing a 10% by mass vitamin B water dispersion liquid, and the independent holes C were formed by using a dispenser (available from Musashi Engineering, Inc., product name: SUPER ΣxIII) to discharge polyethylene glycol 2000 heated and melted at 60 degrees C.

—Sheet Laminate Production Example B4—

A sheet laminate B4 was produced in the same manner as in Sheet laminate production example B3, except that unlike in Sheet laminate production example B3, the number of layers laminated was changed from 2 to 5.

—Sheet Laminate Production Example B5—

A sheet laminate B5 was produced in the same manner as in Sheet laminate production example B3, except that unlike in Sheet laminate production example B3, the biocompatible material of the base material 1 was changed from gelatin to agar and the material of the adhesive layer was changed to agar.

—Sheet Laminate Production Example B6—

A sheet laminate B6 was produced in the same manner as in Sheet laminate production example B3, except that unlike in Sheet laminate production example B3, the material contained in the independent holes $A_1$ was changed to sugar and the material contained in the independent holes $A_2$ was changed to salt.

—Sheet Laminate Production Example B7—

A sheet laminate B7 was produced in the same manner as in Sheet laminate production example B3, except that unlike in Sheet laminate production example B3, the biocompatible material of the base material 1 was changed from gelatin to polylactic acid (PLA).

—Sheet Laminate Production Example B8—

A sheet laminate B8 was produced in the same manner as in Sheet laminate production example B7, except that unlike in Sheet laminate production example B7, the material contained in the independent holes C was changed from polyethylene glycol 2000 (PEG2000) to polylactic acid (PLA).

—Sheet Laminate Production Example B9—

A sheet laminate B9 was produced in the same manner as in Sheet laminate production example B3, except that unlike in Sheet laminate production example B3, the material contained in the independent holes C and the material of the adhesive layer were changed from polyethylene glycol 2000 (PEG2000) to polyvinyl pyrrolidone (PVP).

—Sheet Laminate Production Example B10—

Figure 6:
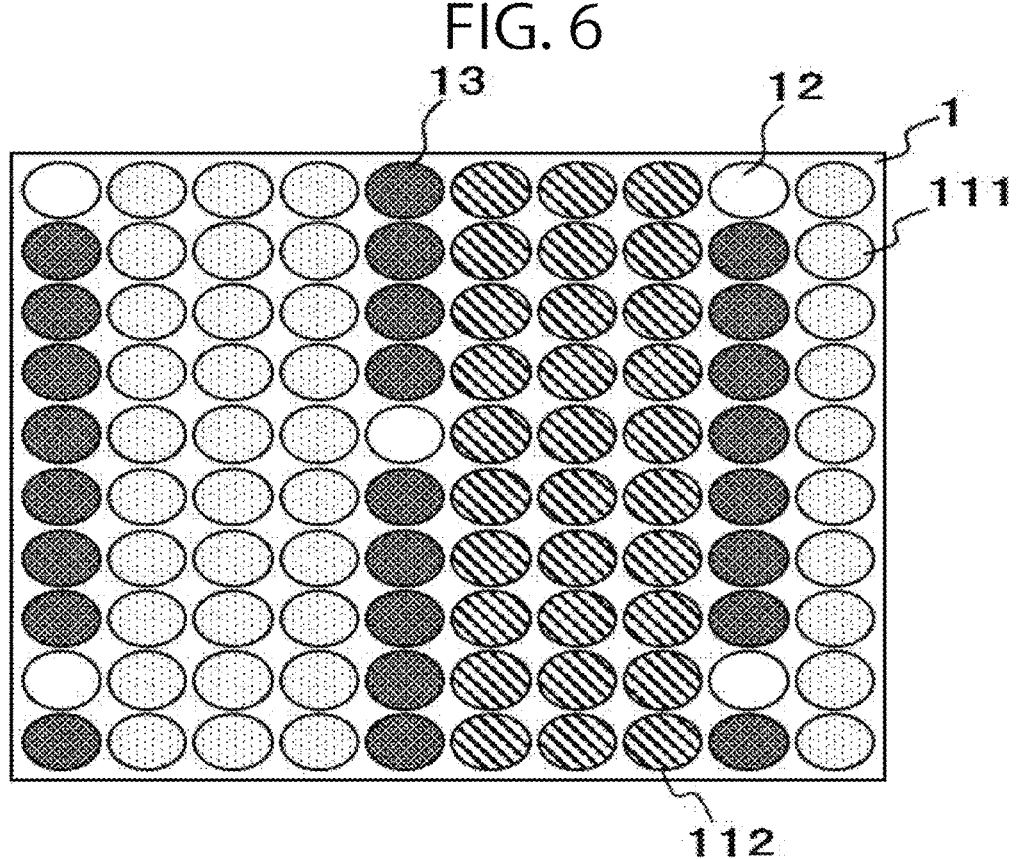
FIG. 6 is a view illustrating another example of a sheet according to an embodiment of the present disclosure.

A sheet laminate B10 was produced in the same manner as in Sheet laminate production example B3, except that unlike in Sheet laminate production example B3, the ratio of the number of independent holes A was set to 70, the ratio of the number of independent holes B was set to 5, and the ratio of the number of independent holes C was set to 25 in the arrangement illustrated in FIG. 6.

—Sheet Laminate Production Example B11—

Figure 7:
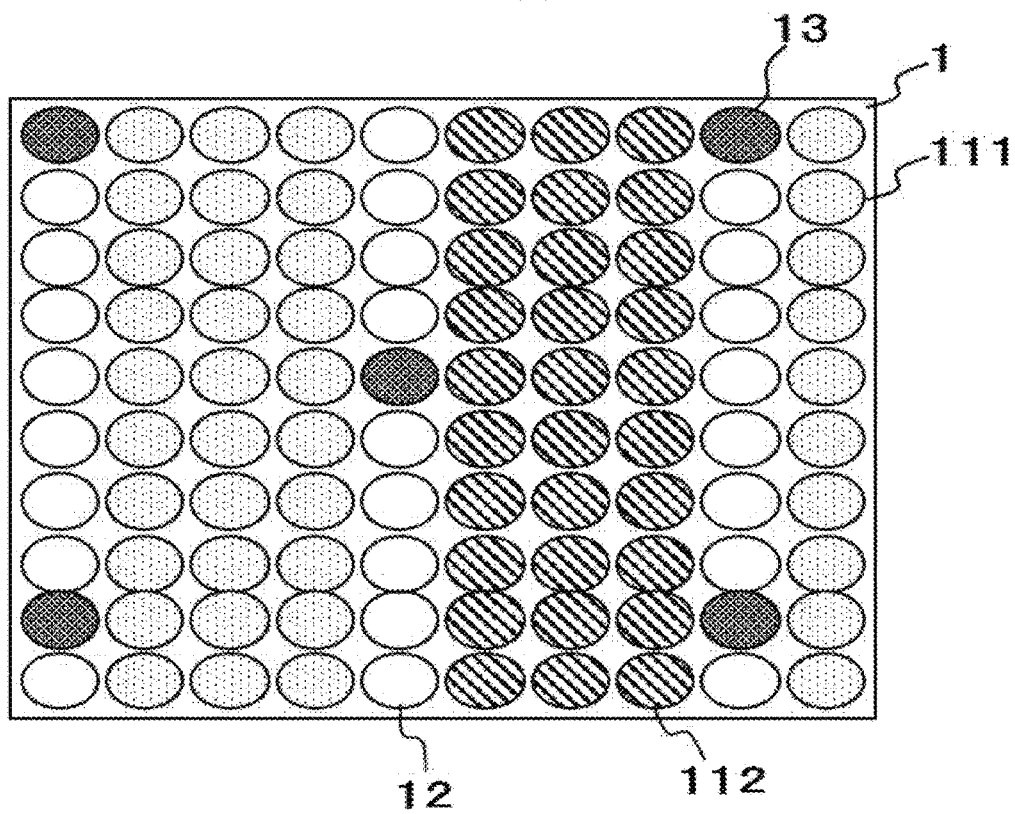
FIG. 7 is a view illustrating another example of a sheet according to an embodiment of the present disclosure.

A sheet laminate B11 was produced in the same manner as in Sheet laminate production example B3, except that unlike in Sheet laminate production example B3, the ratio of the number of independent holes A was set to 70, the ratio of the number of independent holes B was set to 25, and the ratio of the number of independent holes C was set to 5 in the arrangement illustrated in FIG. 7.

—Sheet Laminate Production Example B12—

Figure 8:
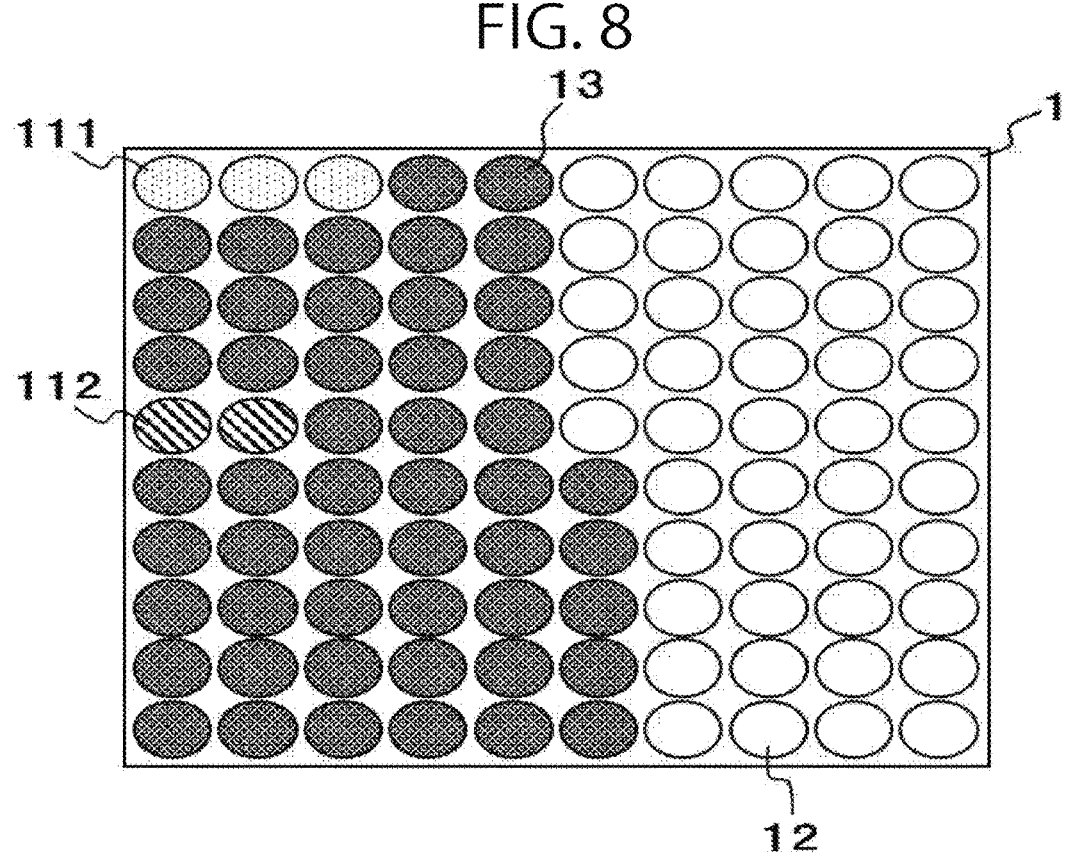
FIG. 8 is a view illustrating another example of a sheet according to an embodiment of the present disclosure.

A sheet laminate B12 was produced in the same manner as in Sheet laminate production example B3, except that unlike in Sheet laminate production example B3, the ratio of the number of independent holes A was set to 5, the ratio of the number of independent holes B was set to 45, and the ratio of the number of independent holes C was set to 50 in the arrangement illustrated in FIG. 8.

—Sheet Laminate Production Example B13—

Figure 9:
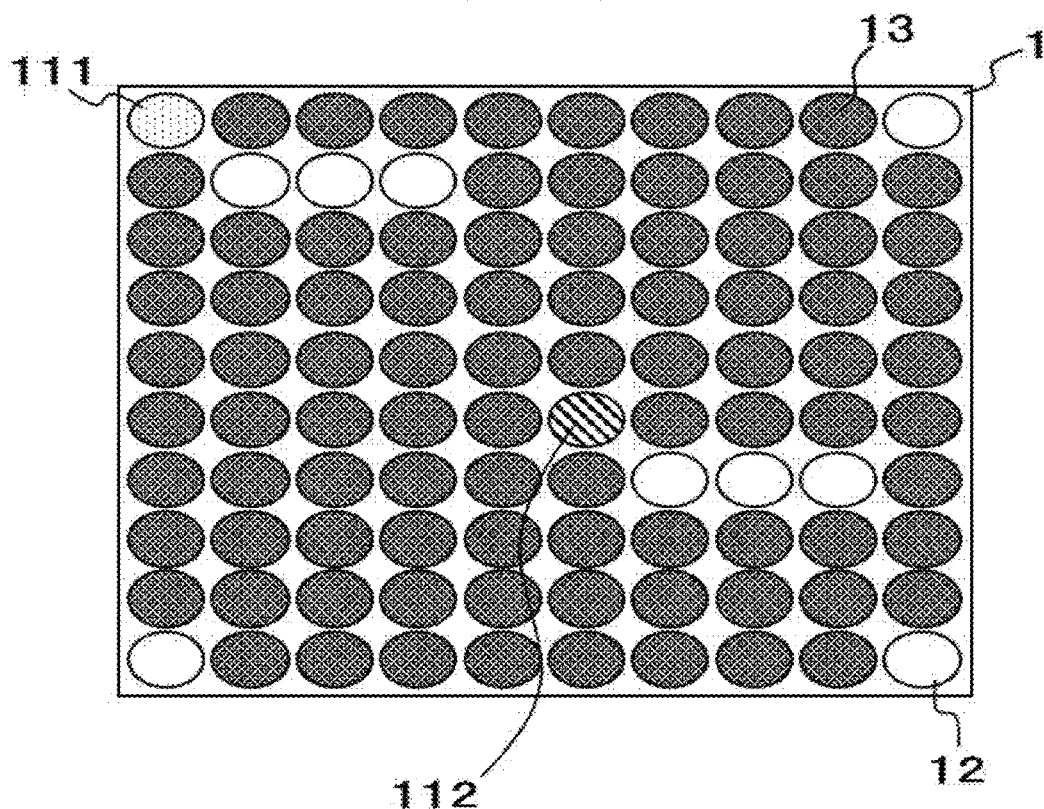
FIG. 9 is a view illustrating another example of a sheet according to an embodiment of the present disclosure.

A sheet laminate B13 was produced in the same manner as in Sheet laminate production example B3, except that unlike in Sheet laminate production example B3, the ratio of the number of independent holes A was set to 2, the ratio of the number of independent holes B was set to 9, and the ratio of the number of independent holes C was set to 89 in the arrangement illustrated in FIG. 9.

—Sheet Laminate Production Example B14—

Figure 10:
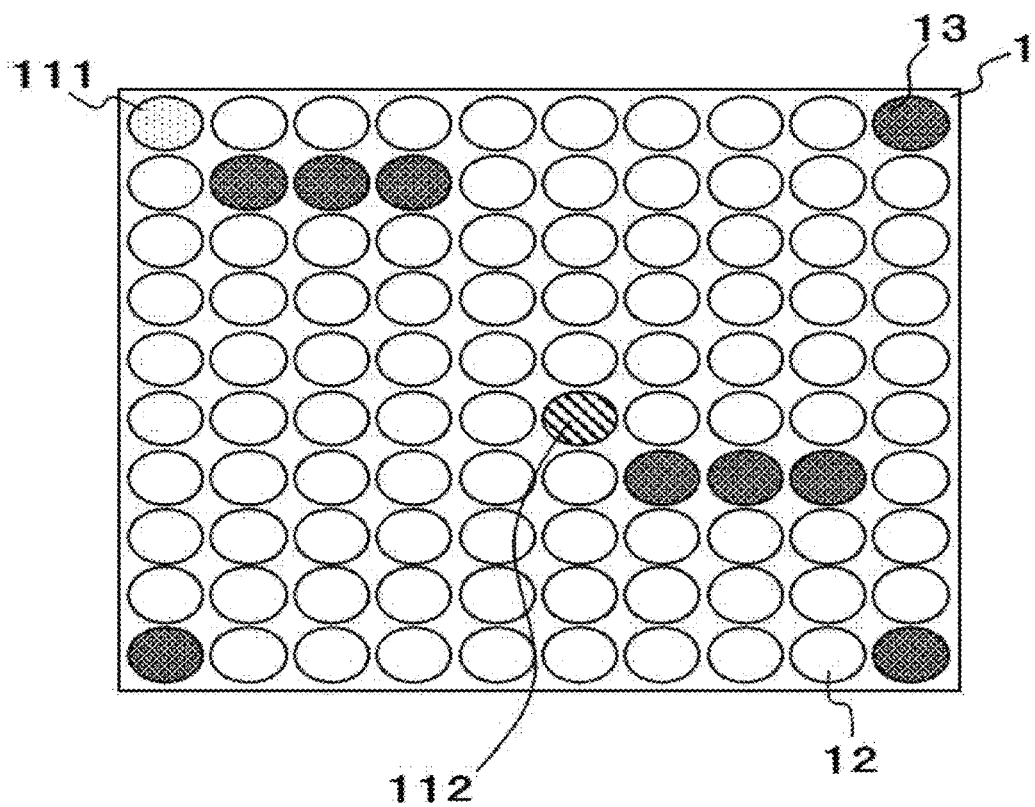
FIG. 10 is a view illustrating another example of a sheet according to an embodiment of the present disclosure.

A sheet laminate B14 was produced in the same manner as in Sheet laminate production example B3, except that unlike in Sheet laminate production example B3, the ratio of the number of independent holes A was set to 2, the ratio of the number of independent holes B was set to 89, and the ratio of the number of independent holes C was set to 9 in the arrangement illustrated in FIG. 10.

—Sheet Laminate Production Example B15—

Figure 11:
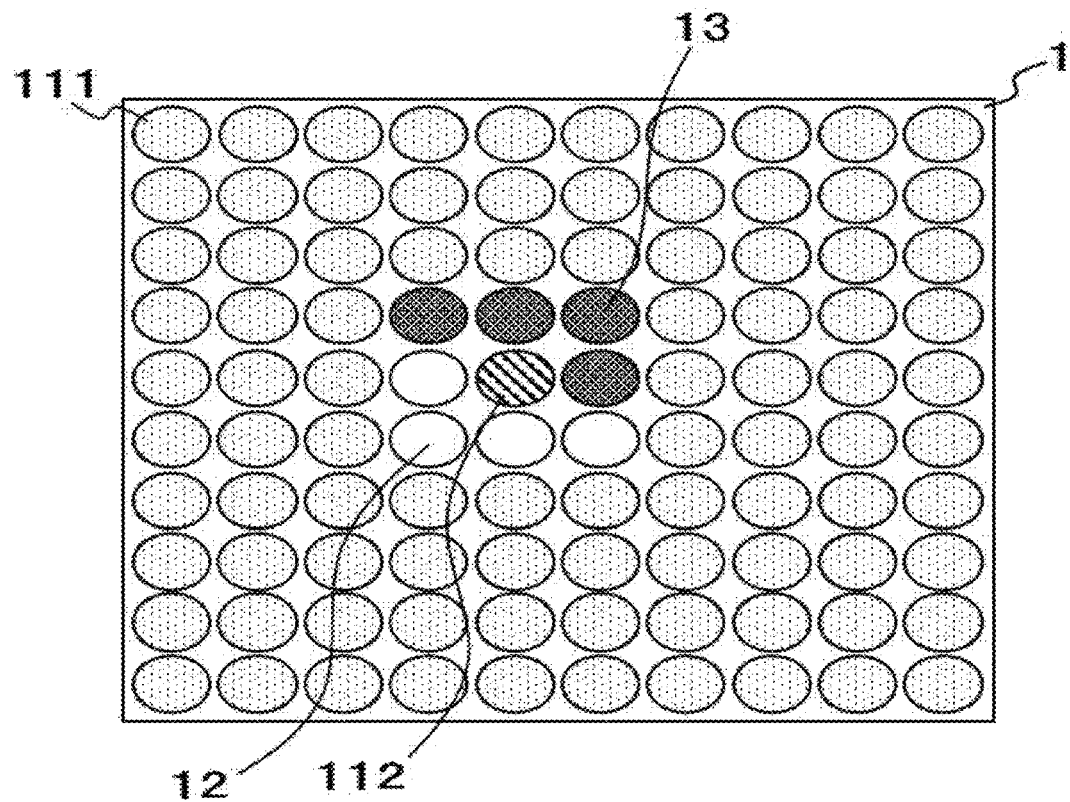
FIG. 11 is a view illustrating another example of a sheet according to an embodiment of the present disclosure.

A sheet laminate B15 was produced in the same manner as in Sheet laminate production example B3, except that unlike in Sheet laminate production example B3, the ratio of the number of independent holes A was set to 92, the ratio of the number of independent holes B was set to 4, and the ratio of the number of independent holes C was set to 4 in the arrangement illustrated in FIG. 11.

—Sheet Laminate Production Example B16—

Figure 12:
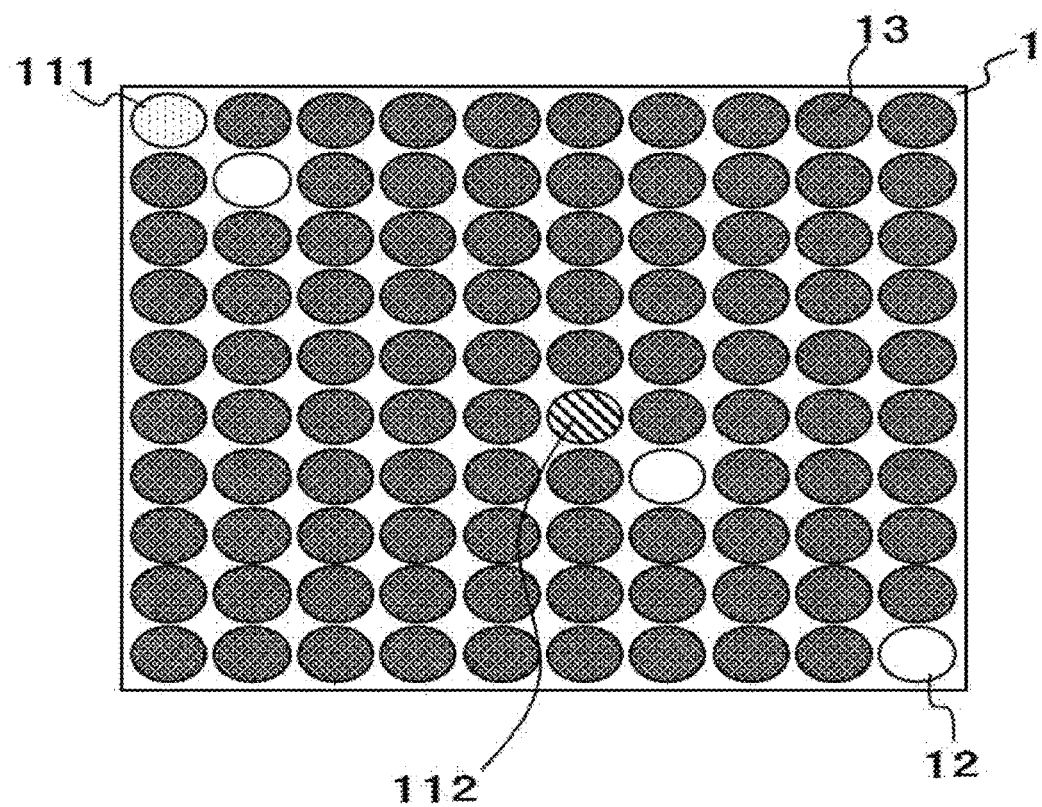
FIG. 12 is a view illustrating another example of a sheet according to an embodiment of the present disclosure.

A sheet laminate B16 was produced in the same manner as in Sheet laminate production example B3, except that unlike in Sheet laminate production example B3, the ratio of the number of independent holes A was set to 2, the ratio of the number of independent holes B was set to 3, and the ratio of the number of independent holes C was set to 95 in the arrangement illustrated in FIG. 12.

—Sheet Laminate Production Example B17—

Figure 13:
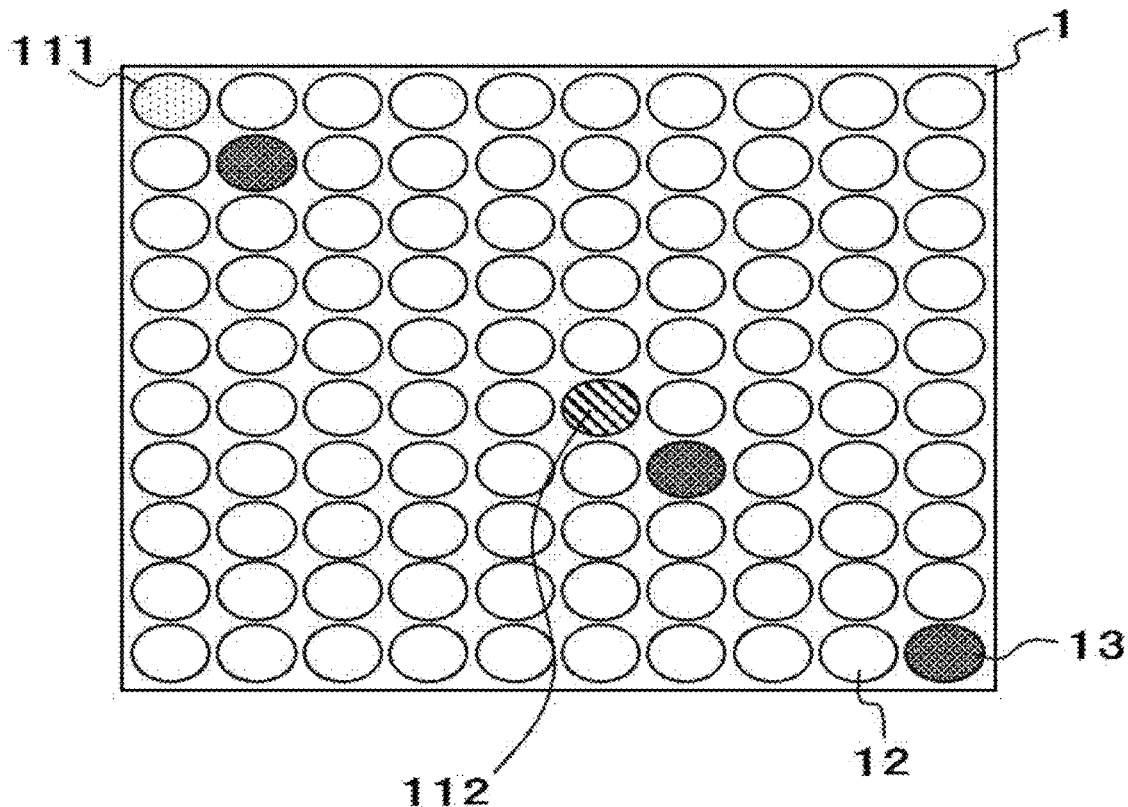
FIG. 13 is a view illustrating another example of a sheet according to an embodiment of the present disclosure.

A sheet laminate B17 was produced in the same manner as in Sheet laminate production example B3, except that unlike in Sheet laminate production example B3, the ratio of the number of independent holes A was set to 2, the ratio of the number of independent holes B was set to 95, and the ratio of the number of independent holes C was set to 3 in the arrangement illustrated in FIG. 13.

—Sheet Laminate Production Example B18—

A sheet laminate B18 was produced in the same manner as in Sheet laminate production example B3, except that unlike in Sheet laminate production example B3, the ratio of the number of independent holes A was set to 82, the ratio of the number of independent holes B was set to 14, and the ratio of the number of independent holes C was set to 4 in the arrangement illustrated in FIG. 14.

—Sheet Laminate Production Example B19—

A sheet laminate B19 was produced in the same manner as in Sheet laminate production example B18, except that unlike in Sheet laminate production example 18, a 10% by mass vitamin B water dispersion liquid was contained in all independent holes A.

—Sheet Laminate Production Example B20—

A sheet laminate B20 was produced in the same manner as in Sheet laminate production example B19, except that unlike in Sheet laminate production example B19, no adhesive layer was provided.

—Sheet Laminate Production Example B21—

A sheet laminate B21 was produced in the same manner as in Sheet laminate production example B1, except that unlike in Sheet laminate production example B1, the shortest distance between the centers of adjacent holes was set to 0.2 mm, to obtain an opening ratio of 28% as in the production of the base material 2.

—Sheet Laminate Production Example B22—

A sheet laminate B22 was produced in the same manner as in Sheet laminate production example B2, except that unlike in Sheet laminate production example B2, the independent holes at the positions of the independent holes B were changed to independent holes C containing polyethylene glycol 2000.

—Sheet Laminate Production Example B23—

A sheet laminate B23 was produced in the same manner as in Sheet laminate production example B2, except that unlike in Sheet laminate production example B2, a 10% by mass vitamin B water dispersion liquid was contained in all independent holes in the sheet.

—Sheet Laminate Production Example B24—

A sheet laminate B24 was produced in the same manner as in Sheet laminate production example B23, except that unlike in Sheet laminate production example B23, the number of layers laminated was changed from 2 to 5.

—Sheet Laminate Production Example B25—

A sheet laminate B25 was produced in the same manner as in Sheet laminate production example B23, except that unlike in Sheet laminate production example B23, no adhesive layer was provided.

—Sheet Laminate Production Example B26—

A sheet laminate B26 was produced in the same manner as in Sheet laminate production example B21, except that unlike in Sheet laminate production example B21, no independent holes B were provided.

The configurations of the sheet laminates B1 to B26 produced in Sheet laminate production examples B1 to B26 described above are presented in Table 3.

TABLE 3

| Sheet laminate production example | Sheet laminate No. | Number of layers laminated | Base material Biocompatible material | Additive (glycerin) (% by mass) | Independent holes A $A_1$ Material contained | $A_2$ Material contained | Ratio of number of holes A (%) |
|---|---|---|---|---|---|---|---|
| Production ex. | B1 | 2 | Gelatin | 20 | Vitamin B | — | 70 |
| | B2 | 2 | Gelatin | 20 | Vitamin B | Vitamin K | 70 |
| | B3 | 2 | Gelatin | 20 | Vitamin B | Vitamin K | 49 |
| | B4 | 5 | Gelatin | 20 | Vitamin B | Vitamin K | 49 |
| | B5 | 2 | Agar | 20 | Vitamin B | Vitamin K | 49 |
| | B6 | 2 | Gelatin | 20 | Sugar | Salt | 49 |
| | B7 | 2 | PLA | 20 | Vitamin B | Vitamin K | 49 |
| | B8 | 2 | PLA | 20 | Vitamin B | Vitamin K | 49 |
| | B9 | 2 | Gelatin | 20 | Vitamin B | Vitamin K | 49 |
| | B10 | 2 | Gelatin | 20 | Vitamin B | Vitamin K | 70 |
| | B11 | 2 | Gelatin | 20 | Vitamin B | Vitamin K | 70 |
| | B12 | 2 | Gelatin | 20 | Vitamin B | Vitamin K | 5 |
| | B13 | 2 | Gelatin | 20 | Vitamin B | Vitamin K | 2 |
| | B14 | 2 | Gelatin | 20 | Vitamin B | Vitamin K | 2 |
| | B15 | 2 | Gelatin | 20 | Vitamin B | Vitamin K | 92 |
| | B16 | 2 | Gelatin | 20 | Vitamin B | Vitamin K | 2 |
| | B17 | 2 | Gelatin | 20 | Vitamin B | Vitamin K | 2 |
| | B18 | 2 | Gelatin | 20 | Vitamin B | Vitamin K | 82 |
| | B19 | 2 | Gelatin | 20 | Vitamin B | — | 82 |
| | B20 | 2 | Gelatin | 20 | Vitamin B | — | 82 |
| | B21 | 2 | Gelatin | 20 | Vitamin B | — | 42 |
| | B22 | 2 | Gelatin | 20 | Vitamin B | Vitamin K | 70 |
| | B23 | 2 | Gelatin | 20 | Vitamin B | — | 100 |
| | B24 | 5 | Gelatin | 20 | Vitamin B | — | 100 |
| | B25 | 2 | Gelatin | 20 | Vitamin B | — | 100 |
| | B26 | 2 | Gelatin | 20 | Vitamin B | — | 100 |

| Sheet laminate production example | Independent holes B Material contained | Ratio of number of holes B (%) | Independent holes C Material contained | Ratio of number of holes C (%) | Sum of ratios of numbers of holes B and holes C (%) | Adhesive layer Material |
|---|---|---|---|---|---|---|
| Production ex. | B1 | Hollow | 30 | — | — | 30 | PEG2000 |
| | B2 | Hollow | 30 | — | — | 30 | Gelatin |
| | B3 | Hollow | 30 | PEG2000 | 21 | 51 | PEG2000 |
| | B4 | Hollow | 30 | PEG2000 | 21 | 51 | PEG2000 |
| | B5 | Hollow | 30 | PEG2000 | 21 | 51 | Agar |
| | B6 | Hollow | 30 | PEG2000 | 21 | 51 | PEG2000 |
| | B7 | Hollow | 30 | PEG2000 | 21 | 51 | PEG2000 |
| | B8 | Hollow | 30 | PLA | 21 | 51 | PLA |
| | B9 | Hollow | 30 | PVP | 21 | 51 | PVP |
| | B10 | Hollow | 5 | PEG2000 | 25 | 30 | PEG2000 |
| | B11 | Hollow | 25 | PEG2000 | 5 | 30 | PEG2000 |
| | B12 | Hollow | 45 | PEG2000 | 50 | 95 | PEG2000 |
| | B13 | Hollow | 9 | PEG2000 | 89 | 98 | PEG2000 |
| | B14 | Hollow | 89 | PEG2000 | 9 | 98 | PEG2000 |

TABLE 3-continued

| | | | | | | |
|---|---|---|---|---|---|---|
| B15 | Hollow | 4 | PEG2000 | 4 | 8 | PEG2000 |
| B16 | Hollow | 3 | PEG2000 | 95 | 98 | PEG2000 |
| B17 | Hollow | 95 | PEG2000 | 3 | 98 | PEG2000 |
| B18 | Hollow | 14 | PEG2000 | 4 | 18 | PEG2000 |
| B19 | Hollow | 14 | PEG2000 | 4 | 18 | PEG2000 |
| B20 | Hollow | 14 | PEG2000 | 4 | 18 | — |
| B21 | Hollow | 51 | — | — | 51 | PEG2000 |
| B22 | — | — | PEG2000 | 30 | 30 | Gelatin |
| B23 | — | — | — | — | — | Gelatin |
| B24 | — | — | — | — | — | Gelatin |
| B25 | — | — | — | — | — | — |
| B26 | — | — | — | — | — | PEG2000 |

Next, the sheet laminates obtained in Sheet laminate production examples B1 to B26 were measured and evaluated in the manners described in "thickness of sheet laminate", "evaluation of water disintegrability", "evaluation of elution of bioactive substance", "evaluation of mechanical strength", and "evaluation of transportation durability" below. The results are presented in Table 4.

<Measurement of Thickness of Sheet Laminate>

The thickness of the sheet laminate was measured with a constant pressure thickness gauge available from Teclock Corporation and compliant with JISK6783. The measurement was conducted three times, and the average was employed as thickness.

<Evaluation of Water Disintegrability>

A stirring bar having a size of 18 mm×6 mm (in diameter) and pure water (100 mL) were put in a 200 mL tall beaker (available from Iwaki & Co., Ltd.), to stir the pure water at a rotation speed of 200 rpm. A sample obtained by forming the sheet laminate into a circle having a diameter of 10 mm was put in a hemispherical bowl-shaped container having a radius of 20 mm and a hook. The bowl-shaped container had been formed by machining 18 mesh stainless steel having a wire diameter of 0.5 mm. The bowl-shaped container having a hook was hooked on the 200 mL tall beaker, to immerse the sample in the water. Seeing a timing at which the sample was entirely immersed as 0 seconds, the time taken afterwards for the sheet laminate to break into respective sheets was obtained as a measurement. The test was conducted three times, to calculate the average as a disintegration time and evaluate the disintegration time according to the evaluation criteria described below.

[Evaluation Criteria]
10 points: Shorter than 10 seconds
8 points: 10 seconds or longer but shorter than 60 seconds
6 points: 60 seconds or longer but shorter than 180 seconds
4 points: 180 seconds or longer but shorter than 300 seconds
2 points: 300 seconds or longer but shorter than 900 seconds
0 points: 900 seconds or longer <Evaluation of Elution of Bioactive Substance>

A stirring bar having a size of 18 mm×6 mm (in diameter) and pure water (100 mL) were put in a 200 mL tall beaker (available from Iwaki & Co., Ltd.), to stir the pure water at a rotation speed of 200 rpm. A sample obtained by forming the sheet laminate into a circle having a diameter of 10 mm was put in a hemispherical bowl-shaped container having a radius of 20 mm and a hook. The bowl-shaped container had been formed by machining 18 mesh stainless steel having a wire diameter of 0.5 mm. The bowl-shaped container having a hook was hooked on the 200 mL tall beaker, to immerse the sample in the water. The thickness of the sample was arbitrary. Seeing a timing at which the sample was entirely immersed as 0 seconds, the refractive index of the liquid in the beaker after 60 minutes was measured, to calculate the concentration as a measurement and measure the elution rate according to the formula described below. The test was conducted three times, to evaluate the average elution rate according to the evaluation criteria described below.

$$\text{Elution rate} = (\text{measurement})/(\text{theoretical concentration when the sample completely eluted}) \times 100 \quad \text{Formula 1}$$

[Evaluation Criteria]
10 points: 90% or higher but 100% or lower
0 points: Lower than 90%

<Mechanical Strength Testing>

The breaking strength of the sheet laminate formed into a circle having a diameter of 10 mm was measured with a tablet hardness tester. The thickness of the sheet laminate was arbitrary. The strength of the sheet laminate was measured at a breaking point, which was a timing at which visually observable cracking or chipping occurred in the sheet laminate. The test was conducted three times, and the average value of strength was divided by the thickness, to obtain a breaking strength. The breaking strength was evaluated according to the evaluation criteria described below.

[Evaluation Criteria]
10 points: 0.5 kg/mm or greater
5 points: 0.14 kg/mm or greater but less than 0.5 kg/mm
2 points: 0.05 kg/mm or greater but less than 0.14 kg/mm
0 points: Less than 0.05 kg/mm <Transportation Durability Testing>

A dropping device used was formed of an acrylic pipe having a length of 1.0 m and an internal diameter of 10 cm and an acrylic plate coupled to one end of the acrylic pipe in a manner that the surface of the acrylic plate was orthogonal to the longer-axis direction of the pipe. The end of the dropping device having the acrylic plate was placed on a horizontal table, and the sheet laminate formed into a circle having a diameter of 10 mm was let to freely fall from the open end of the pipe, to visually observe how the landed sheet laminate would be damaged. The test was conducted ten times, and evaluation was performed according to the evaluation criteria described below, to obtain the average as the test result.

[Evaluation Criteria]
0 points: The landed sheet laminate chipped or cracked by 1 mm or greater.
10 points: The landed sheet laminate did not chip or crack by 1 mm or greater.

<Total Evaluation>

The total of the points in each evaluation described above was evaluated according to the evaluation criteria described below.

[Evaluation Criteria]
A: 36 points or greater but 40 points or less
B: 31 points or greater but 35 points or less
C: 26 points or greater but 30 points or less
D: 21 points or greater but 25 points or less
E: 16 points or greater but 20 points or less
F: 15 points or less

TABLE 4

| | | | | Evaluation results | | | | | | | | |
|---|---|---|---|---|---|---|---|---|---|---|---|---|
| | | | Thickness of sheet laminate | Evaluation of water disintegrability | | Evaluation of elution | | Evaluation of mechanical strength | | Evaluation of transportation durability | | Total evaluation |
| | | Sheet laminate No. | (mm) | Disintegration time (second) | | Average elution rate (%) | | Breaking strength (kg/mm) | | Number of samples chipped | | Total |
| Ex. | 15 | B1 | 1.7 | 55 | 8 | 95 | 10 | 0.3 | 5 | 1 | 9 | 32 B |
| | 16 | B2 | 2.4 | 65 | 6 | 96 | 10 | 0.1 | 2 | 3 | 8 | 26 C |
| | 17 | B3 | 1.2 | 58 | 8 | 95 | 10 | 0.6 | 10 | 0 | 10 | 38 A |
| | 18 | B4 | 5.8 | 129 | 6 | 90 | 10 | 0.6 | 10 | 0 | 10 | 36 A |
| | 19 | B5 | 1.2 | 132 | 6 | 93 | 10 | 0.4 | 5 | 0 | 10 | 31 B |
| | 20 | B6 | 1.2 | 56 | 8 | 98 | 10 | 0.6 | 10 | 0 | 10 | 38 A |
| | 21 | B7 | 1.2 | 251 | 4 | 91 | 10 | 0.6 | 10 | 0 | 10 | 34 B |
| | 22 | B8 | 1.3 | 602 | 2 | 90 | 10 | 0.6 | 10 | 0 | 10 | 32 B |
| | 23 | B9 | 1.2 | 173 | 6 | 92 | 10 | 0.6 | 10 | 0 | 10 | 36 A |
| | 24 | B10 | 1.2 | 230 | 4 | 92 | 10 | 0.6 | 10 | 0 | 10 | 34 B |
| | 25 | B11 | 1.2 | 144 | 6 | 94 | 10 | 0.4 | 5 | 1 | 9 | 30 C |
| | 26 | B12 | 1.2 | 40 | 8 | 94 | 10 | 0.6 | 10 | 0 | 10 | 38 A |
| | 27 | B13 | 1.2 | 297 | 4 | 91 | 10 | 0.7 | 10 | 0 | 10 | 34 B |
| | 28 | B14 | 1.2 | 37 | 8 | 96 | 10 | 0.3 | 5 | 3 | 7 | 30 C |
| | 29 | B15 | 1.2 | 299 | 4 | 92 | 10 | 0.4 | 5 | 1 | 9 | 28 C |
| | 30 | B16 | 1.2 | 870 | 2 | 90 | 10 | 0.7 | 10 | 0 | 10 | 32 B |
| | 31 | B17 | 1.2 | 79 | 6 | 94 | 10 | 0.3 | 5 | 3 | 7 | 28 C |
| | 32 | B18 | 1.2 | 174 | 6 | 94 | 10 | 0.4 | 5 | 0 | 10 | 31 B |
| | 33 | B19 | 1.2 | 177 | 6 | 95 | 10 | 0.4 | 5 | 0 | 10 | 31 B |
| | 34 | B20 | 1.0 | 35 | 8 | 95 | 10 | 0.4 | 5 | 1 | 9 | 32 B |
| Comp. Ex. | 2 | B21 | 0.8 | 926 | 0 | 78 | 0 | 0.5 | 10 | 0 | 10 | 20 E |
| | 3 | B22 | 1.2 | 15 minutes or longer | 0 | 10 | 0 | 0.6 | 10 | 0 | 10 | 20 E |
| | 4 | B23 | 1.2 | 854 | 2 | 10 | 0 | 0.4 | 5 | 3 | 7 | 14 E |
| | 5 | B24 | 5.8 | 890 | 2 | 10 | 0 | 0.4 | 5 | 3 | 7 | 14 E |
| | 6 | B25 | 1.0 | 295 | 4 | 20 | 0 | 0.4 | 5 | 4 | 6 | 15 E |
| | 7 | B26 | 0.8 | 1,350 | 0 | 74 | 0 | 0.4 | 5 | 1 | 9 | 14 F |

Aspects of the present disclosure are, for example, as follows.

<1> A sheet including
a base material comprising a biocompatible material and having at least two independent holes, and a bioactive substance,
wherein the independent holes include at least one independent hole A containing the bioactive substance,
wherein the independent holes include at least one independent hole B containing no bioactive substance,
wherein a maximum diameter of the independent holes is less than 0.2 mm.

<2> The sheet according to <1>, wherein the independent holes further include at least one independent hole C containing a thermoplastic material.

<3> The sheet according to <1> or <2>,
wherein, when one of the independent holes A is an independent hole $A_1$ containing a first bioactive substance and another one of the independent holes A located closest to the one of the independent holes A is an independent hole $A_2$ containing a second bioactive substance different from the first bioactive substance, one or more other independent holes be arranged between the one of the independent holes A and the another one of the independent holes A.

<4> The sheet according to <3>,
wherein the independent hole B and the independent hole C are arranged between the independent hole $A_1$ containing the first bioactive substance and the independent hole $A_2$ containing the second bioactive substance.

<5> The sheet according to any one of <2> to <4>,
wherein a ratio of a number of the independent hole B to a number of all the independent holes is 5% or greater but 90% or less,
wherein a ratio of a number of the independent hole C to the number of all the independent holes is 5% or greater but 90% or less, and
wherein a sum of the ratio of the number of the independent hole B and the ratio of the number of the independent holes C is 20% or greater but less than 100%.

<6> The sheet according to any one of <1> to <5>,
wherein the base material has a brittle portion at which strength is lower than other portions, and
wherein the brittle portion is provided in a predetermined shape.

<7> The sheet according to <6>,
wherein the brittle portion is at least any one of the independent hole B and a perforated portion.

<8> The sheet according to any one of <1> to <7>,
wherein the biocompatible material is at least any one selected from the group consisting of gelatin, agar, gum Arabic, and polysaccharides.

<9> The sheet according to any one of <2> to <8>,
wherein the thermoplastic material is at least any one selected from the group consisting of polyethylene glycol and modified bodies of polyethylene glycol, polyvinyl alcohol and modified bodies of polyvinyl alcohol, and polyvinyl pyrrolidone and modified bodies of polyvinyl pyrrolidone.

<10> The sheet according to any one of <1> to <9>,
wherein the independent hole B is a hollow concave.

<11> A sheet laminate including
sheets laminated with each other,
wherein each of the sheets is the sheet according to any one of <1> to <10>.

<12> A sheet laminate including
sheets laminated with each other,
wherein each of the sheets includes a base material comprising a biocompatible material and having at least two independent holes, and a bioactive substance,
wherein the independent holes include at least one independent hole A containing the bioactive substance,
wherein the independent holes include at least one independent hole B containing no bioactive substance.

<13> The sheet laminate according to <12>, wherein the independent holes further include at least one independent hole C containing a thermoplastic material.

<14> The sheet laminate according to <12> or <13>,
wherein, when one of the independent holes A is an independent hole $A_1$ containing a first bioactive substance and another one of the independent holes A located closest to the one of the independent holes A is an independent hole $A_2$ containing a second bioactive substance different from the first bioactive substance, one or more other independent holes are between the one of the independent holes A and the another one of the independent holes A.

<15> The sheet laminate according to <13> or <14>,
wherein a ratio of a number of the independent hole B to a number of all independent holes is 5% or greater but 90% or less,
wherein a ratio of a number of the independent hole C to the number of all independent holes is 5% or greater but 90% or less, and
wherein a sum of the ratio of the number of the independent hole B and the ratio of the number of the independent hole C is 20% or greater but less than 100%.

<16> The sheet laminate according to any one of <11> to <15>, further including
an adhesive layer between the sheets,
wherein the adhesive layer contains at least any one selected from the group consisting of the biocompatible material and a thermoplastic material.

<17> A pharmaceutical drug including
at least any one selected from the group consisting of the sheet according to any one of <1> to <10> and the sheet laminate according to any one of <11> to <16>.

<18> The pharmaceutical drug according to <17>,
wherein the pharmaceutical drug is at least any one selected from the group consisting of tablet, peptizer, drop, lozenge, film preparation, capsule, suppository, intercalating agent, and patch.

<19> A sheet producing method for producing the sheet according to any one of <1> to <10>, the sheet producing method including
forming the independent hole A and the independent hole B.

<20> The sheet producing method according to <19>, further including
forming the independent hole C.

<21> The sheet producing method according to <19> or <20>, further including
forming the sheet into a predetermined shape.

<22> A sheet producing apparatus configured to produce the sheet according to any one of <1> to <10>, the sheet producing apparatus including
an independent hole forming unit configured to form the independent hole A and the independent hole B.

<23> A sheet laminate producing method for producing the sheet laminate according to any one of <11> to <16>, the sheet laminate producing method including:
forming the independent hole A and the independent hole B; and
laminating the sheet.

<24> The sheet laminate producing method according to <23>, further including
forming the independent hole C.

<25> The sheet laminate producing method according to <23> or <24>, further including
forming the sheet into a predetermined shape.

<26> The sheet laminate producing method according to any one of <23> to <25>,
wherein the independent hole A is formed by filling the bioactive substance in the at least one of the independent holes by at least any one of an inkjet method and a dispenser method.

<27> The sheet laminate producing method according to any one of <23> to <26>,
wherein the independent hole C is formed by filling the thermoplastic material in any of the at least two independent holes by at least any one of an inkjet method and a dispenser method.

<28> A sheet laminate producing apparatus configured to produce the sheet laminate according to any one of <11> to <16>, the sheet laminate producing apparatus including:
an independent hole forming unit configured to form the independent hole A and the independent hole B; and
a laminating unit configured to laminate the sheets.

<29> The sheet laminate producing apparatus according to <28>, further including
an independent hole forming unit configured to form the independent hole C.

<30> The sheet laminate producing apparatus according to <28> or <29>, further including
a shaping unit configured to form the sheet into a desired shape.

The sheet according to any one of <1> to <10>, the sheet laminate according to any one of <11> to <16>, the pharmaceutical drug according to <17> or <18>, the sheet producing method according to any one of <19> to <21>, the sheet producing apparatus according to <22>, the sheet laminate producing method according to any one of <23> to <27>, and the sheet laminate producing apparatus according to any one of <28> to <30> can solve the various problems in the related art and achieve the object of the present disclosure.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

The invention claimed is:
1. A sheet, comprising:
a base material comprising a biocompatible material, the base material having at least three independent holes; and a bioactive substance,
wherein the independent holes include at least one independent hole A containing the bioactive substance,
wherein the independent holes include at least one independent hole B containing no bioactive substance,
wherein the maximum diameter of the independent holes is less than 0.2 mm,
wherein the independent holes further comprise at least one independent hole C containing a thermoplastic material and no bioactive substance.

2. The sheet according to claim 1,
wherein one of the independent holes A is an independent hole $A_1$ containing a first bioactive substance and another one of the independent holes A located closest to the independent hole $A_1$ is an independent hole $A_2$ containing a second bioactive substance different from the first bioactive substance, wherein at least one independent hole B and at least one independent hole C are arranged between the independent hole $A_1$ and the independent holes $A_2$.

3. The sheet according to claim 1,
wherein the ratio of the number of the independent hole B to the number of all the independent holes is 5% or greater but 90% or less,
wherein the ratio of the number of the independent hole C to the number of all the independent holes is 5% or greater but 90% or less, and
wherein the sum of the ratio of the number of the independent hole B and the ratio of the number of the independent hole C is 20% or greater but less than 100%.

4. The sheet according to claim 1,
wherein the base material has a brittle portion at which strength is lower than other portions.

5. The sheet according to claim 4,
wherein the brittle portion is at least any one of the independent hole B and a perforated portion.

6. The sheet according to claim 1,
wherein the biocompatible material comprises at least any one selected from the group consisting of gelatin, agar, gum Arabic, and polysaccharides.

7. The sheet according to claim 1,
wherein the thermoplastic material comprises at least any one selected from the group consisting of polyethylene glycol and derivatives of polyethylene glycol, polyvinyl alcohol and derivatives of polyvinyl alcohol, and polyvinyl pyrrolidone and derivatives of polyvinyl pyrrolidone.

8. A sheet laminate, comprising:
sheets laminated with each other,
wherein each of the sheets is the sheet according to claim 1.

9. A sheet laminate, comprising:
sheets laminated with each other,
wherein each of the sheets comprises:
a base material comprising a biocompatible material and having at least three independent holes; and
a bioactive substance,
wherein the independent holes include at least one independent hole A containing the bioactive substance,
wherein the independent holes include at least one independent hole B containing no bioactive substance, and
wherein the independent holes further comprise at least one independent hole C containing a thermoplastic material and no bioactive substance.

10. The sheet laminate according to claim 9,
wherein one of the independent holes A is an independent hole $A_1$ containing a first bioactive substance and another one of the independent holes A located closest to the independent hole $A_1$ is an independent hole $A_2$ containing a second bioactive substance different from the first bioactive substance, wherein one or more other independent holes B are arranged between the independent hole $A_1$ and the independent holes $A_2$.

11. The sheet laminate according to claim 9,
wherein the ratio of the number of the independent hole B to the number of all the independent holes is 5% or greater but 90% or less,
wherein the ratio of the number of the independent hole C to the number of all the independent holes is 5% or greater but 90% or less, and
wherein the sum of the ratio of the number of the independent hole B and the ratio of the number of the independent hole C is 20% or greater but less than 100%.

12. The sheet laminate according to claim 8, further comprising:
an adhesive layer between the sheets,
wherein the adhesive layer comprises at least one selected from the group consisting of the biocompatible material and a thermoplastic material.

13. A sheet according to claim 1, wherein the bioactive substances comprise a pharmaceutical drug.

14. The sheet according to claim 13,
wherein the pharmaceutical drug is in the form of at least one form selected from the group consisting of tablet, drop, lozenge, film preparation, capsule, suppository, and patch.

15. The sheet according to claim 1, wherein the bioactive substance comprises a vitamin.

16. The sheet according to claim 2, wherein the first bioactive substance comprises Vitamin B and the second biocompatible substance comprises Vitamin K, and the thermoplastic material comprises polyethylene glycol.

* * * * *